United States Patent [19]
Askin et al.

[11] Patent Number: 5,164,525
[45] Date of Patent: Nov. 17, 1992

[54] SYNTHETIC PROCESS FOR FK-506 TYPE MACROLIDE INTERMEDIATES

[75] Inventors: David Askin, Edison; Ralph P. Volante, East Windsor; Daisy Joe, Union; Ichiro Shinkai, Westfield, all of N.J.

[73] Assignee: Merck & Co., Inc., Rahway, N.J.

[21] Appl. No.: 374,508

[22] Filed: Jun. 30, 1989

[51] Int. Cl.$^5$ .............................. C07F 7/08; C07F 7/18
[52] U.S. Cl. .................................. 556/444; 556/445; 568/670; 568/630
[58] Field of Search ................ 556/444, 445; 568/670, 568/630

[56] References Cited

U.S. PATENT DOCUMENTS 5,011,943  4/1991  Wang .............................. 556/444 X

FOREIGN PATENT DOCUMENTS 0364031  4/1990  European Pat. Off. .

OTHER PUBLICATIONS

J. Am. Chem. Soc., 109, 5031 (1987).
J. Am. Chem. Soc., 111, 1157 (1989).

*Primary Examiner*—Paul F. Shaver
*Attorney, Agent, or Firm*—Robert J. North; Charles M. Caruso

[57] ABSTRACT

A process for the conversion of FK-506 (I,R=allyl;1) to FK-525 (XV) and analogous 23-membered ring macrolides differing in the C.1-N.7 segment of the molecule (e.g. XVI) and is also applicable to the analogs FK-523 (XVII) and FK-520 (XVIII). The overall process consists of three stages: (a) initial degradation of the primary macrolide to an acyclic fragment containing a selectively protected C.10–C.34 framework with a protected aldehyde function at C.10 and a free hydroxyl function at C.26, (b) reacylation of the C.26 hydroxyl function with an appropriately N-protected alpha-amino acid moiety, and (c) reintroduction of the C.8 and C.9 carbons followed by regeneration of the FK-macrolide system.

13 Claims, 1 Drawing Sheet

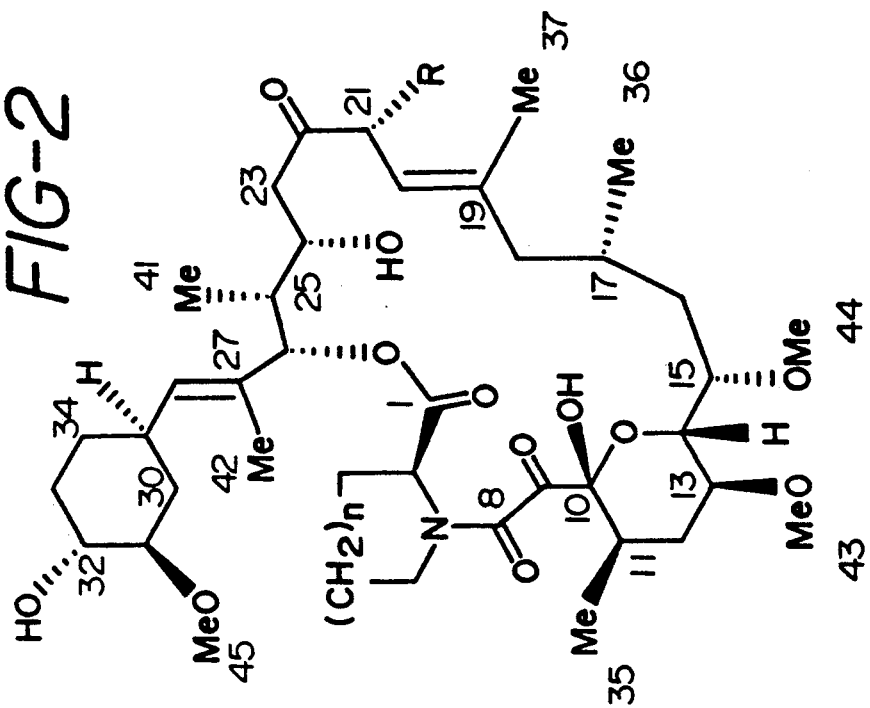
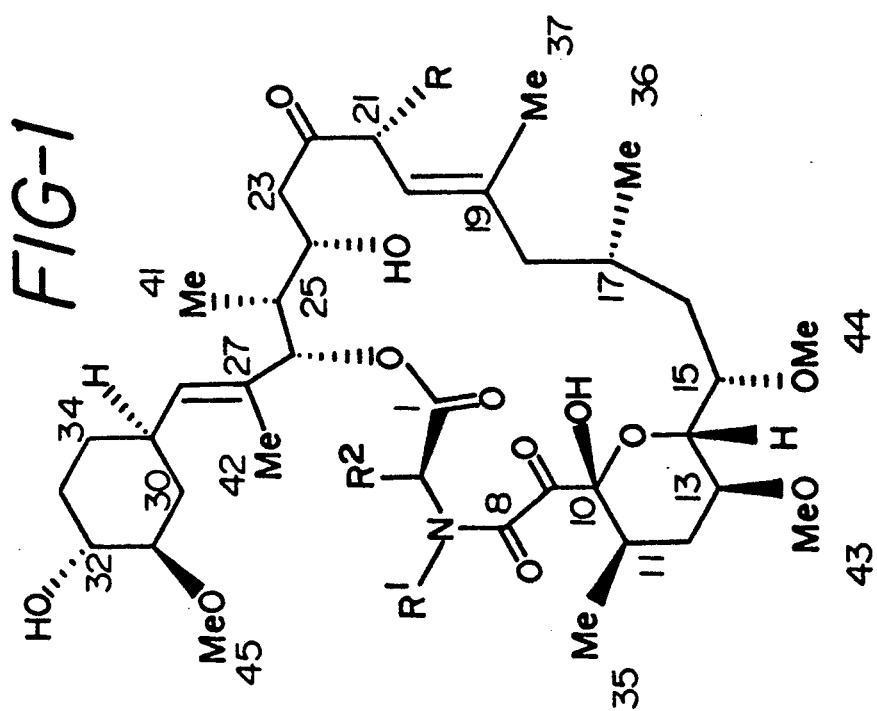
I   R=ALLYL, n=2
XV  R=ALLYL, n=1
XVII  R=ETHYL, n=2
XVIII  R=METHYL, n=2

SYNTHETIC PROCESS FOR FK-506 TYPE MACROLIDE INTERMEDIATES

BACKGROUND OF THE INVENTION

1. Field of the Invention

This invention relates to a new synthetic process for producing macrolide immunosuppressant FK-506 type precursor intermediates.

2. Brief Disclosures in the Art

The novel 23-membered tricyclo-macrolide FK-506 isolated and characterized by Tanaka, Kuroda, and co-workers, see JACS, 109, pp. 5031, 1987, and EPO Publication No. 0,184,162, has been shown to possess exceptional immunosuppressive activity. The potential usefulness of such an agent in bone marrow and organ transplantations coupled with its unique structural features has prompted many in the field to initiate an effort towards the total synthesis of FK-506 (1).

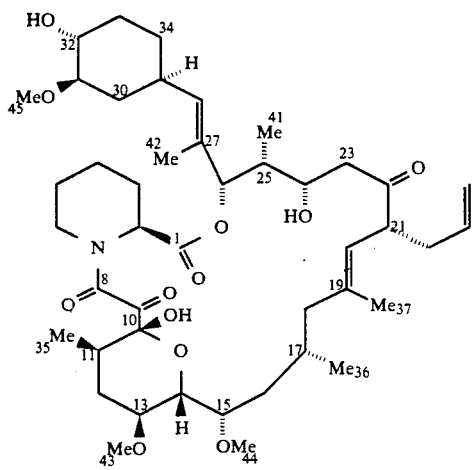

A total synthesis of FK-506 has been achieved by Ichiro Shinkai's Process Chemistry Group at Merck & Co., Inc. by R. Volante, D. Askin, et al. as published in *J. Am. Chem. Soc.*, 1989, Vol. 111, 11, p. 1157. A patent application, U.S. Ser. No. 295,877 filed Jan. 11, 1989, claims this synthesis and is hereby incorporated by reference for this particular purpose.

The total synthesis is an extremely elegant and sophisticated work in the field of macrolide chemistry and requires 54 discrete synthetic steps to FK-506 starting from divinyl carbinol[3] and quinic acid[4]. See [3]Askin, D.; Volante, R. P.; Reamer, R. A.; Ryan, K. M.; Shinkai, I., *Tetrahedron Lett.*, 1988, 29, p. 277, and [4]Mills, S.; Desmond, R.; Reamer, R. A.; Volante, R. P.; Shinkai, I., *Tetrahedron Lett.*, 1988, 28, p. 281.

However, to make other potential immunosuppressant derivatives of FK-506 via this synthetic scheme would be very laborious and particularly those derivatives having a different moiety in the $C_1$-$N_7$ position. It would be desirable to possess a short, convenient process to synthesize FK-506 type macrolides from a readily obtainable intermediate in high yield.

There are no known degradation routes disclosed in the literature from FK-506 to a useful synthetic intermediate. In particular, it is not disclosed how to cleave the C.9, C.10 bond cleanly and in high yield, selectively protect the many alcohol functions and selectively adjust C.10 to the aldehyde oxidation state protected as the labile dimethyl acetal. Furthermore, it is not disclosed as to a method by which the C.26-OH could be deacylated, since all attempts to deacylate C.26-OH with C.22 as the ketone leads to decomposition via a retroaldol fragmentation. See Tanaka, H.; Kuroda, A.; Marusawa, H.; Hatanaka, H.; Kino, T.; Goto, T.; Hashimoto, M.; Taga, T., *J. Am. Chem. Soc.*, 1987, p. 5031.

What is needed in the art is a convenient, relatively low multistep synthesis of an FK-506 degradation intermediate to synthesize other FK-506 type macrolides having different $C_1$-$N_7$ moieties.

SUMMARY OF THE INVENTION

We have discovered a short, ten step convenient route to the versatile intermediate 11, starting with FK-506, as depicted below, which can be used to produce other $C_1$-$N_7$ FK-506 type macrolides, including FK-525. The overall yield from the starting material (FK-506) to 11 is 12%, which means that only 5-6 g of FK-506 is necessary to produce 1 gram of 11.

This route has the ability to prepare quantities of about 1 g of the intermediate 11 in a laboratory setting without the use of special large scale apparatus. By contrast, a period of several months is required for the synthesis of 1 g of 11 based on the above-described total synthesis.

In accordance with the invention, there is provided a compound of the formula:

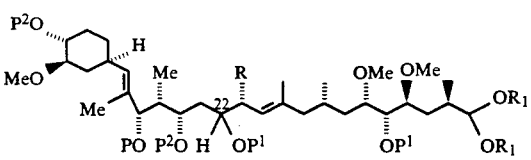

wherein $P/P^1/P^2$ are independently defined as H or tri(hydrocarbo)silyl, wherein said hydrocarbo groups are independently chosen from $C_1$-$C_4$ linear or branched alkyl, phenyl or benzyl, such that P can be selectively removed in the presence of $P^1/P^2$ and R is selected from allyl, propyl, ethyl or methyl, and $R_1$ is methyl or ethyl.

Further provided is a process for degrading an FK-506 type macrolide to a useful intermediate therefor comprising the steps of:

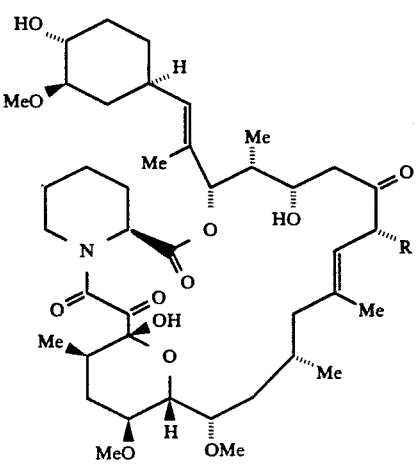

a) contacting I, where R is selected from allyl, methyl, ethyl or propyl, with a silylating agent in the presence of an amine hydrogen acceptor to form II;

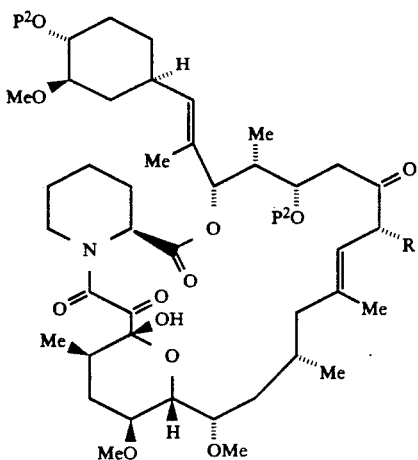

II b) contacting II with Pb(OAc)$_4$ in a dry inert organic solvent containing methanol at a temperature in the range of 10°–40° C. to form III;

III

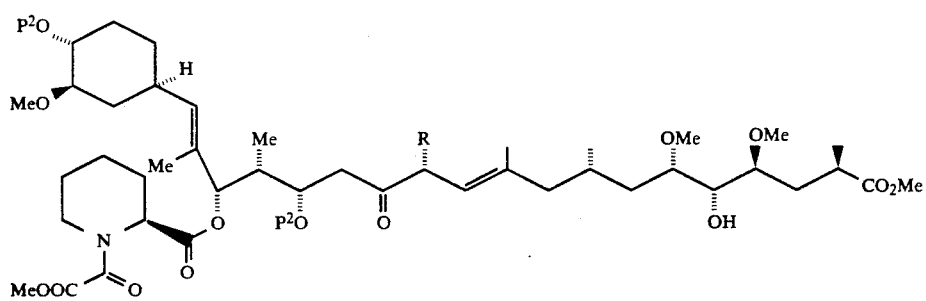

c) contacting III with a silylating agent at 0°–10° C. in the presence of an organic amine hydrogen acceptor to form V;

V

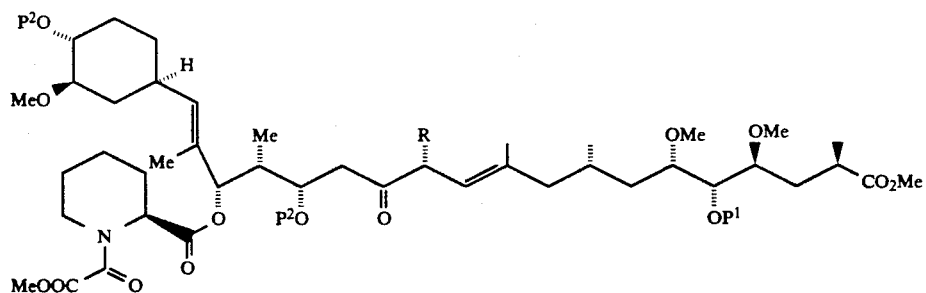

d) contacting V with LiAlH$_4$ at 0°–5° C. for a sufficient time to form the triols VI (R/S);

VI

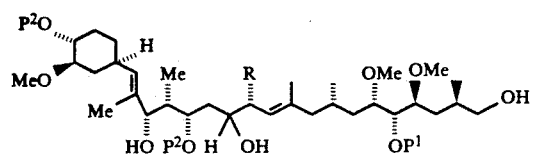

e) contacting the triols VI (R/S) with silylating agent at −10° to 0° C. for a sufficient time to form the alcohol VII (R/S);

VII

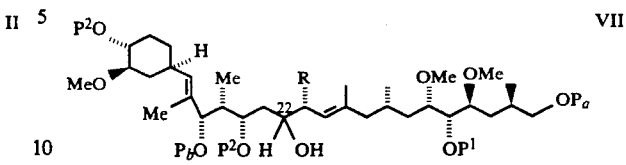

f) contacting alcohol VII (R/S) with silylating agent in the presence of an organic amine hydrogen acceptor at a temperature in the range of 0°–10° C. for a sufficient time to form the ether VIII (R/S);

VIII

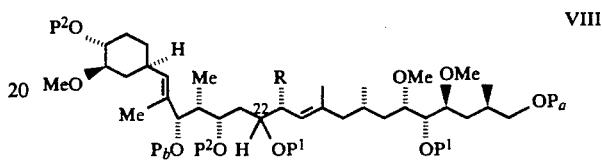

g) contacting VIII with aqueous acetic acid at 25°–50° C. to form the primary alcohols IX, 22(S) and 22(R);

IX

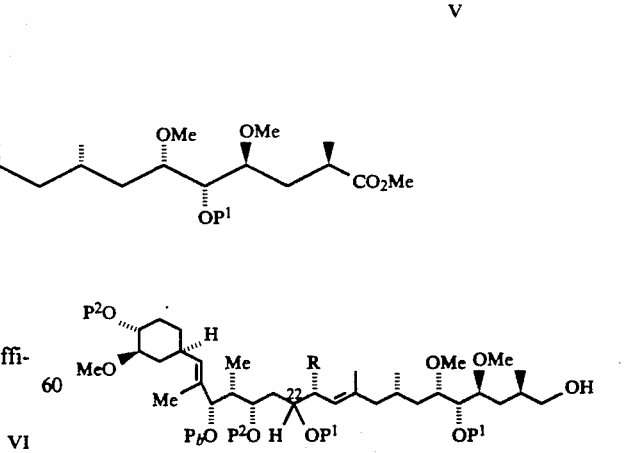

h) contacting IX with oxalyl chloride, DMSO and an organic amine at a temperature in the range of about −80° to −60° C. or alternatively CrO$_3$-pyridine complex at about 25° C. in a dry inert organic solvent for a sufficient time to form X;

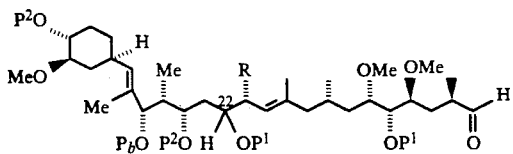

X i) contacting X with methanol, trialkylorothoformate and pyridinium p-toluenesulfonate at 0°-10° C. in a dry organic solvent for a sufficient time to form XI;

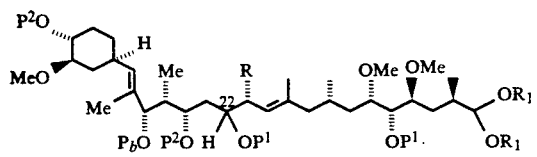

XI wherein P/P¹/P² are independently defined as H or tri(hydrocarbo)silyl, and $P_a$ and $P_b$ are either H or P, and wherein said hydrocarbo groups are independently chosen from $C_1$-$C_4$ linear or branched alkyl, phenyl or benzyl, such that P can be selectively removed in the presence of P¹, P², or both, and $R_1$ is methyl or ethyl.

BRIEF DESCRIPTION OF THE INVENTION AND PREFERRED EMBODIMENTS

The invention described herein concerns the synthesis of a versatile synthetic intermediate 11 for the preparation of FK-506 type macrolides and may be readily understood by reference to generalized Flow Charts A and B, and the specific process for FK-506 as depicted in Flow Charts A¹ and B¹.

This process degrades an FK type macrolide, i.e., FK-506, in ten steps to a C.10-C.34 fragment with the C.10 position at the aldehyde oxidation level protected as a dialkylacetal, e.g. dimethylacetal, and the C.26 hydroxyl group selectively exposed for acylation with an appropriate N-protected, secondary amino-acid, e.g. N-t-Boc-L-proline.

FLOW CHART A

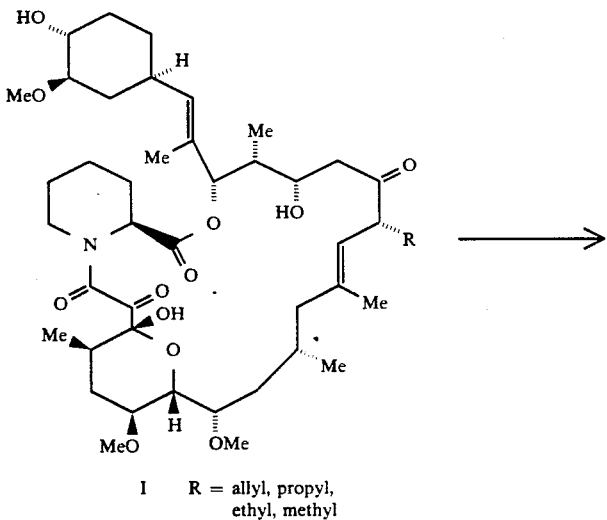

I   R = allyl, propyl, ethyl, methyl

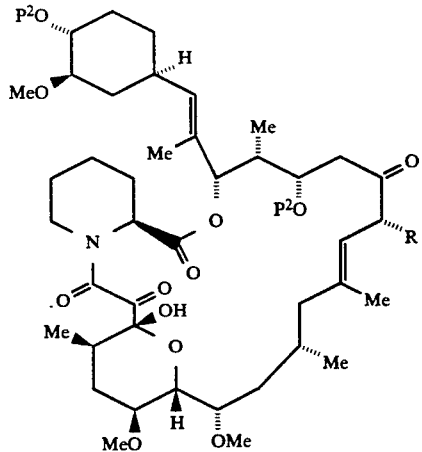

II

-continued
FLOW CHART A
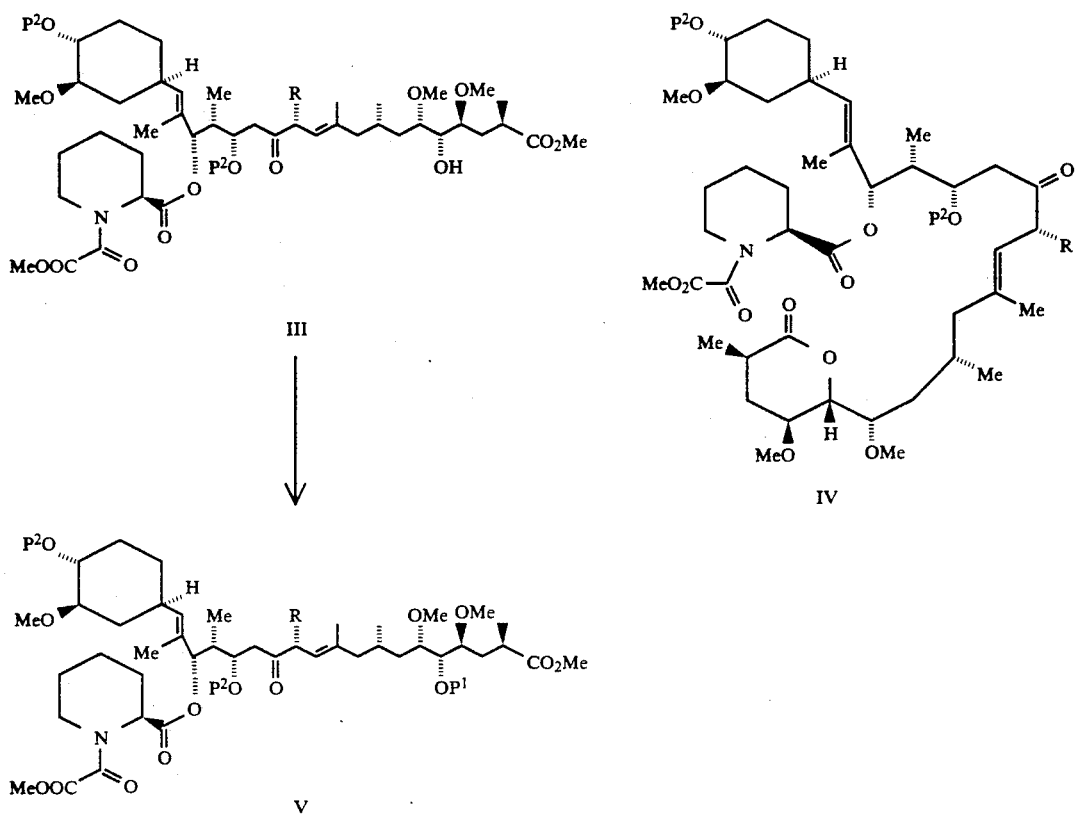
FLOW CHART B
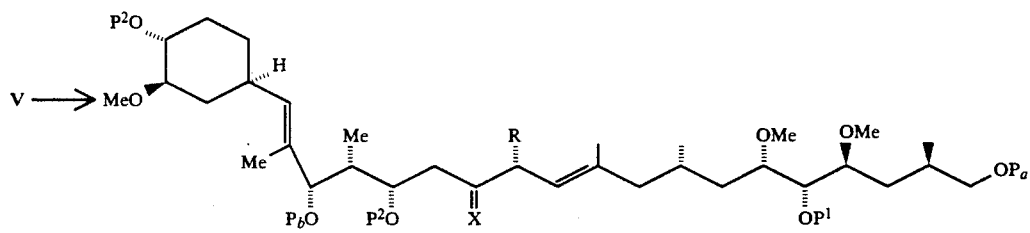
VI (R, S) $P_a = P_b = H$; X = H, OH
VII (R, S) $P_a = P_b = P$; X = H, OH
VIII (R, S) $P_a = P_b = P$; X = H, $OP^1$
IX (R, S) $P_a = H$; $P_b = P$; X = H, $OP^1$
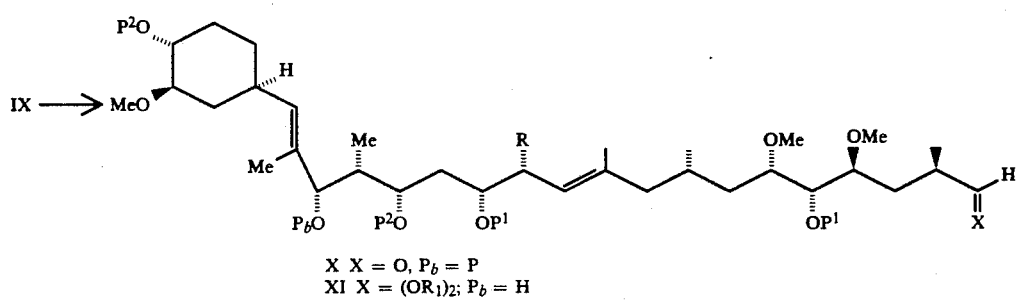
X   X = O, $P_b = P$
XI  X = $(OR_1)_2$; $P_b = H$ -continued
FLOW CHART B
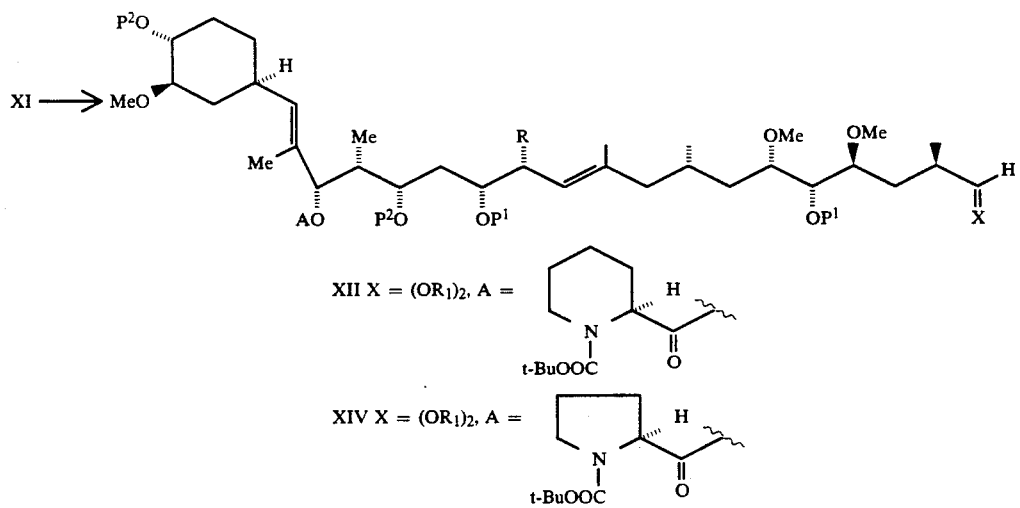
FLOW CHART A¹
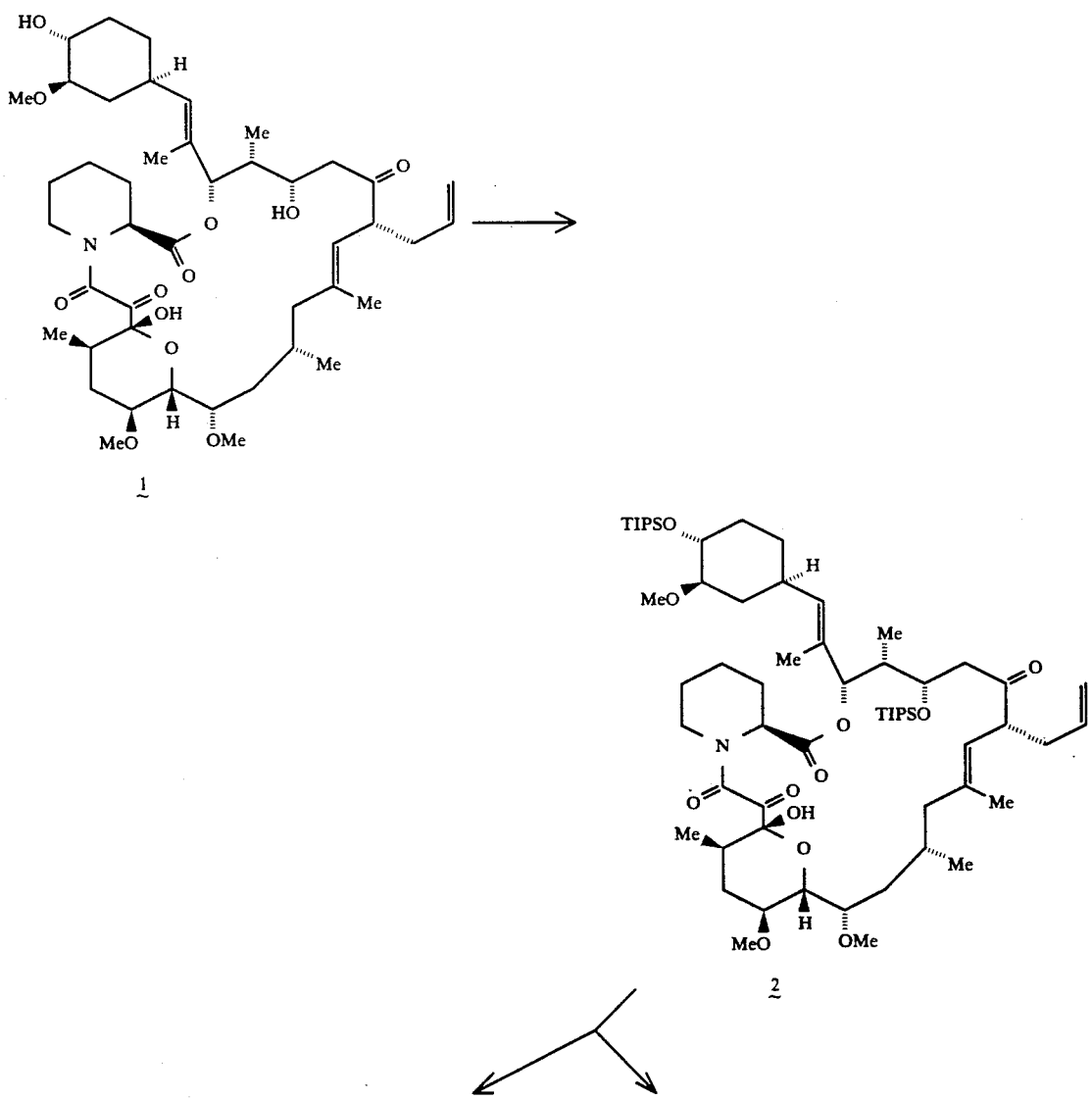

-continued
FLOW CHART A[1]
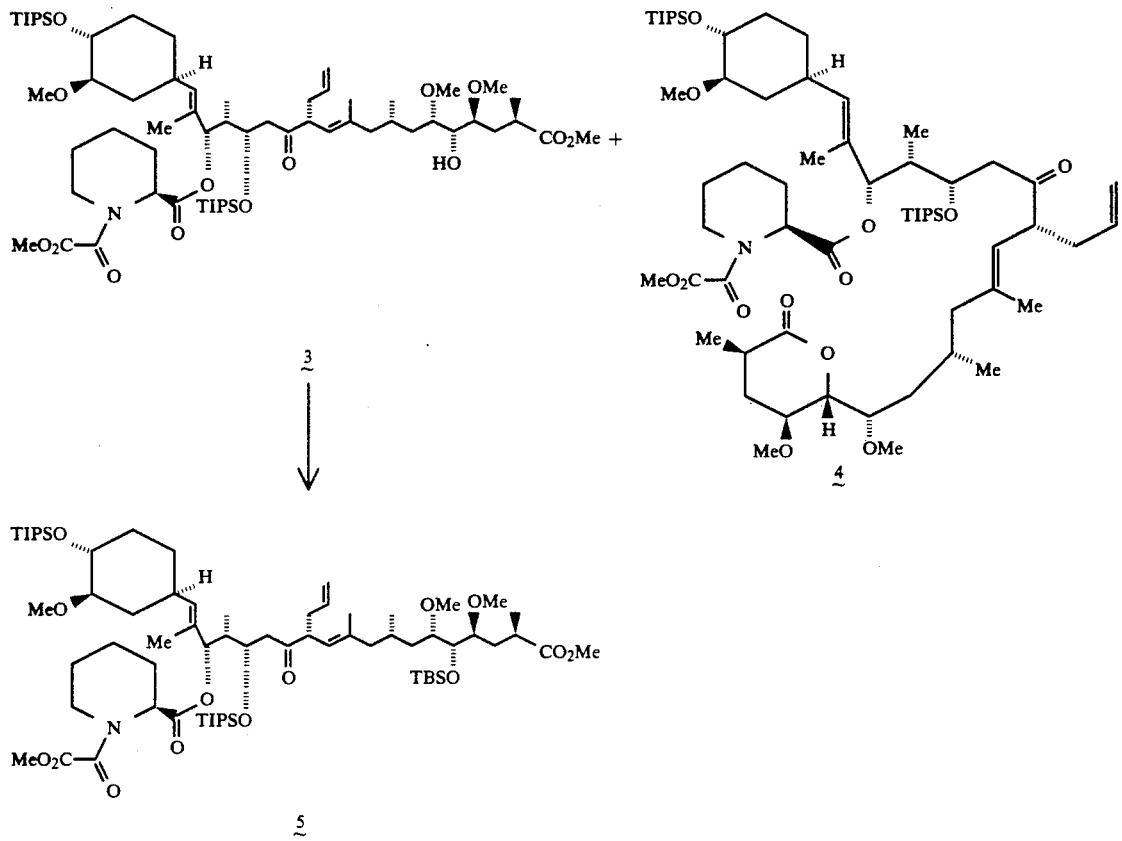
FLOW CHART B[1]
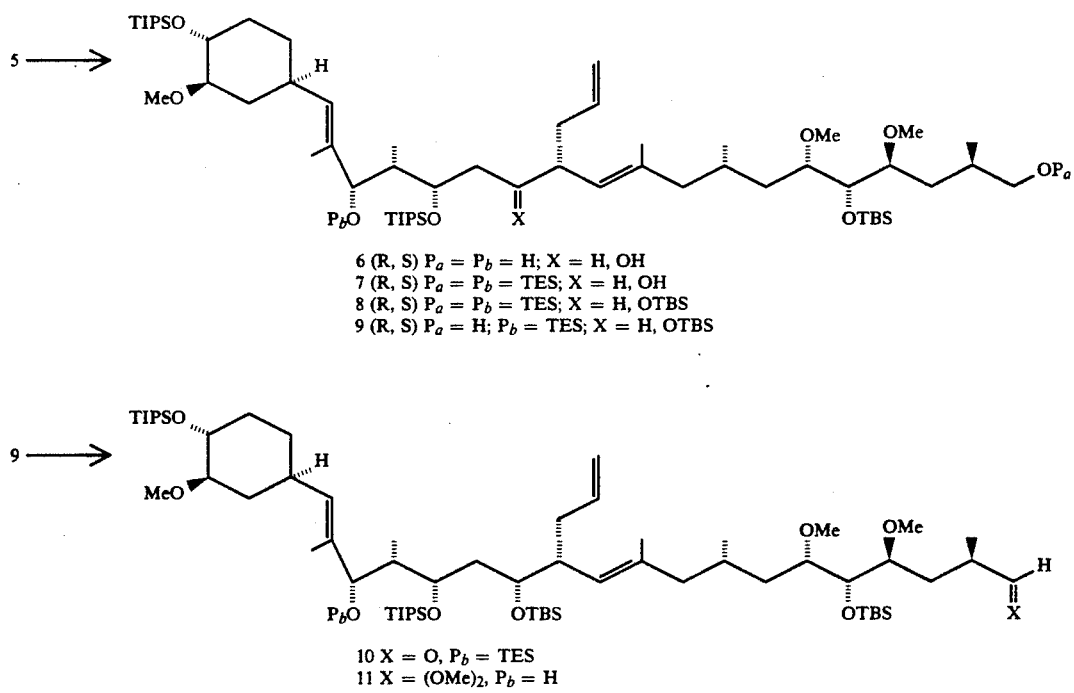
6 (R, S) P_a = P_b = H; X = H, OH
7 (R, S) P_a = P_b = TES; X = H, OH
8 (R, S) P_a = P_b = TES; X = H, OTBS
9 (R, S) P_a = H; P_b = TES; X = H, OTBS
10 X = O, P_b = TES
11 X = (OMe)_2, P_b = H -continued
FLOW CHART B[1]

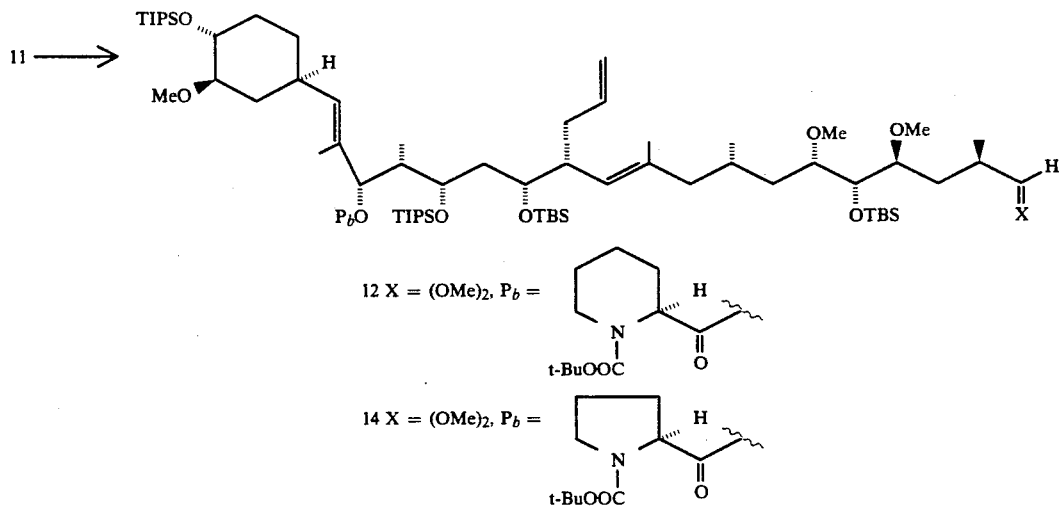

12 X = (OMe)₂, P_b = [piperidine structure with t-BuOOC-N, H, carbonyl]

14 X = (OMe)₂, P_b = [pyrrolidine structure with t-BuOOC-N, H, carbonyl]

The starting FK-506 and corresponding methyl (FK-523), ethyl (FK-520), propyl, and FK-525 (proline) derivatives are known in the art and are described in Fujisawa's EPO Publication No. 0,184,162, supra.

As is seen in Flow Chart A, the initial bis-(trialkylsilylation) of FK-506 type macrolide (I) affords II.

Generally, this step is conducted under anhydrous conditions, e.g. dry nitrogen and a dry inert organic solvent, e.g. dichloromethane, diethylether, dioxane, benzene, toluene, or xylene, in the temperature range of −10° to +25° C., and the presence of an organic nitrogen proton acceptor, e.g. 2,6-lutidine for a sufficient time to produce the bis-protected Product II. Time required generally in the range of 1 to 24 hours. The protecting agent is a triorganosilylating agent for free hydroxyl groups, e.g. triisopropylsilyltriflate (TIPSOTf), preferably being a reagent that provides the triisopropylsilyl group, since it is desired that the C-24 and C-32 hydroxyl groups be protected with the most difficult to remove silyl protecting groups in order that they be removed last.

The bis-protection step is performed with a conventional tri(hydrocarbo)silyl protecting groups P, P[1] and P[2].

P, P[1] and P[2] are selected from conventional trihydrocarbosilyl protecting groups, wherein P can be selectively removed in the presence of P[1] and P[2]; P[1] can be selectively removed in the presence of P[2], by appropriate choice of deprotection reaction conditions as is standard in the art (e.g. choice of reaction temperature, reaction solvent, reagent concentration, reaction time, or strength of reagent in cases of acid catalyzed hydrolysis.

The protecting groups P, P[1] and P[2] can be conventional in the art and are tri(hydrocarbo)silyl, wherein said hydrocarbo group is independently chosen from $C_1-C_4$ linear or branched alkyl, phenyl or benzyl, including mixtures thereof.

Representative examples of tri(hydrocarbo)silyl groups include trimethylsilyl- (TMS), triethylsilyl(TES) as P; isopropyldimethylsilyl-, t-butyldimethylsilyl- (TBS), triisopropylsilyl(TIPS), triphenylsilyl-, tribenzylsilyl- as P[2]; phenyldimethylsilyl-, benzyldimethylsilyl-, diethylisopropylsilyl- as P[1], and the like.

Preferred is where P[2] is triisopropyl (TIPS), P[1] is t-butyldimethylsilyl (TBS) and P is triethylsilyl (TES).

Methods of deprotection are standard in the art and include: (a) removal of P groups, e.g. TES, by acetic acid/water/tetrahydrofuran at 40° C. for about 12 hours; (b) removal of P[1] groups, e.g. TBS, by treating with anhydrous tetrabutylammonium fluoride in THF at 0°-25° C.; (c) removal of P[2] groups, e.g. TIPS, by treating with acetonitrile/50% aqueous HF at 0°-10° C.

The C.9-C.10 bond of II is next cleaved in high yield with lead tetraacetate in an inert solvent mixture, e.g., methanolic benzene, to afford a mixture of the methyl ester III and the corresponding valerolactone IV.

This oxidation step is generally carried out with $Pb(OAc)_4$ as the oxidizing agent in a dry inert solvent, e.g. $C_6-C_8$ aromatic hydrocarbon, i.e., benzene, toluene, xylene or a $C_1-C_4$ alcohol, i.e., methanol, ethanol and the like, at a temperature of about 10°-40° C., preferably 25° C. for a sufficient time to produce III. Varying amounts of valerolactone IV will be formed which can be converted to III by treating with methanol/anhydrous $K_2CO_3$ for a sufficient time to substantially convert IV to III.

The free hydroxyl group in III is next protected by P[1] producing V, a protecting group more easily removable than P[2]. Preferred in this context is the t-butyldimethyl group (TBS) which can be incorporated by treating III in a dry inert organic solvent, e.g. $C_6-C_8$ aromatic $C_2-C_6$ ethers or halogenated $C_1-C_4$ alkane i.e. dichloromethane, with a silylating agent, e.g. TBS triflate and an organic amine proton acceptor, i.e. 2,6-lutidine, at 0°-25° C. for a sufficient time to substantially silylate the free hydroxy group.

Exhaustive hydride reduction of V affords the triols VI (R,S) as, e.g., a 2.5 to 1 mixture of inseparable C.22 epimers with the (R)-epimer predominating. Although only the major (R)-C.22 epimer has been thus far used for the synthesis of FK-506 and congeners, it is reasonably believed that the (S)-C.22 epimer is also useful.

The reduction step is carried out with a strong reducing agent, preferably $LiAlH_4$, in a dry inert organic solvent, e.g. $C_2-C_4$ ether, i.e. tetrahydrofuran, diethylether, and the like, at 0°-25° C., under a dry atmosphere for a sufficient time to substantially reduce the ketone to the secondary alcohol, reduce the ester group to an alcohol and cleave the pipecolinic ester to afford VI.

In a key step, selective protection of the C.10 and C.26 alcohols is achieved with, e.g., TESCl/pyridine to afford the bis-protected, e.g., bis(triethylsilyl ethers) VII (R,S).

VI is then treated with this protecting group P, being more easily removable than P² and P¹, and preferably is triethylsilyl. The conditions generally include treating VI with a silylating agent, e.g. triethylsilylchloride, in an anhydrous, inert solvent, e.g. dichloromethane, diethylether, tetrahydrofuran, in the presence of an amine nitrogen proton acceptor, e.g. 2,6-lutidine, triethylamine, or a solvent such as pyridine can be used accomplishing both goals. The temperature is generally in the range of $-10°$ to $25°$ C. to achieve substantial yields of VII.

The exposed C.22-OH (R and S epimers) is then silyl protected as, for example, the tertbutyldimethylsilyl ether, as described above, to afford VIII (R,S).

Selective deblocking of the terminal primary C.10-silylated ether then gives the chromatographically separable C.22-epimers IX (R) and (S).

The deblocking is carried out in a weak acid mixture, e.g. HOAc/THF/H₂O, at $25°$-$50°$ C., preferably $40°$ C., to produce a substantial yield of the IX (R, S) alcohols.

IX is subjected to Swern oxidizing conditions involving oxalyl chloride, dimethylsulfoxide, and triethylamine, at $-78°$ to $-40°$ C. or CrO₃-pyridine at $25°$ C. in a dry inert solvent, e.g. dichloromethane, for a sufficient time to obtain a substantial yield of the aldehyde X.

X is converted to the dimethylacetal and the ether group at position 26 is deprotected by treatment with triethylorthoformate and a weak acid catalyst, pyridinium p-toluenesulfonate, in a dry inert organic solvent, e.g. THF, methanol, benzene, CH₂Cl₂, and the like, at $0°$-$25°$ C., for a sufficient time to substantially form the key intermediate XI. Note that triethylorthoformate can also be used in place of the trimethyl analog and that the subsequent triethyl analog is also deemed to be covered within the scope of this invention.

XI can be reacted with an N-protected secondary amino acid, e.g. N-t-Boc-L-proline, under the conditions involving the reagent dicyclocarbodiimide and N,N-diethylaminopyridine in an inert dry organic solvent, e.g. dichloromethane at $-50°$ to $-25°$ C., for a sufficient time to form the condensation product, e.g. XIV.

For example, the C.26 alcohol of 11 can be acylated (as designated by P$_b$) with a variety of N-protected amino acids such as N-(tert-butoxycarbonyl)-(S)- pipecolic acid with 1,3-dicyclohexylcarbodiimide/dimethylaminopyridine to afford 12, an intermediate in the total synthesis of FK-506. See Jones, T. K.; Mills, S. G.; Reamer, R. A.; Askin, D.; Desmond, R.; Volante, R. P.; Shinkai, I., *J. Am. Chem. Soc.*, 1989, 111, p. 1157.

Other secondary amino acids (e.g. in their N-protected form, e.g. N-t-Boc) can also be employed in the synthesis starting with the compound 11 condensation step and includes all naturally occurring amino acids and those known synthetic variations in the art which include those of the following formulae:

Acyclic Secondary Amino Acids

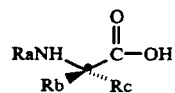

where $R_a = C_1-C_{10}$ alkyl, aryl, or substituted alkyl; $R_b = H$, $C_1-C_{10}$ alkyl, aryl, or substituted alkyl; and $R_c = H$, $C_1-C_{10}$ alkyl, aryl, or substituted alkyl, said substituents, including halo, $C_1-C_4$ alkoxy, e.g. chloro, methoxy, and the like.

Representative examples include N-methyl, N-ethyl, N-benzyl, N-phenyl substituted L- and D-forms (and racemates) of alanine, valine, leucine, isoleucine, phenylalanine, tyrosine, diiodotyrosine, thyroxine, serine, threonine, methionine, cysteine, cystine, aspartic acid, glutamic acid, lysine, arginine, known synthetic variants thereof, sarcosine, and the like;

Cyclic Secondary Amino Acids

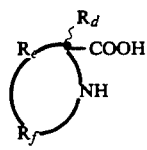

where $R_d = H$, $C_1-C_{10}$ alkyl, aryl or branched alkyl, which may be in the alpha or beta configuration; $R_e$ and $R_f$ are carbon-containing chains joined with NH to form a 4–10 membered carbon-nitrogen ring, which can be saturated, unsaturated or partially unsaturated, can contain one or more O, S or N heteroatoms and which can be ring substituted.

The above secondary amino acids are converted to their N-t-Boc protected form, by conventional procedure, and can be utilized in the place of sarcosine, proline, or pipecolinic acid.

Representative examples include L- and D-forms of proline, hydroxyproline, N-methyltryptophan, N-methylhistidine, 2-pipecolinic acid, known synthetic variants thereof, and the like, wherein said substituents include halo, $C_1-C_4$ alkoxy, i.e. chloro, methoxy, and the like.

Also described is the synthetic sequence for converting the condensation product to the corresponding FK type macrolide. For example, 14 is converted to FK-525.

The above procedure is applicable to all of the FK-506 macrolide family, e.g. FK-506 (R¹=allyl), FK-525 (R¹=allyl), FK-520 (R¹=ethyl), FK-523 (R¹=methyl) and the FK-506 analog where R¹=propyl).

FIGS. 1 and 2 show two FK-506 type macrolides.

The following examples are illustrative of carrying out the instant invention and should not be construed as being a limitation on the scope or spirit of the invention.

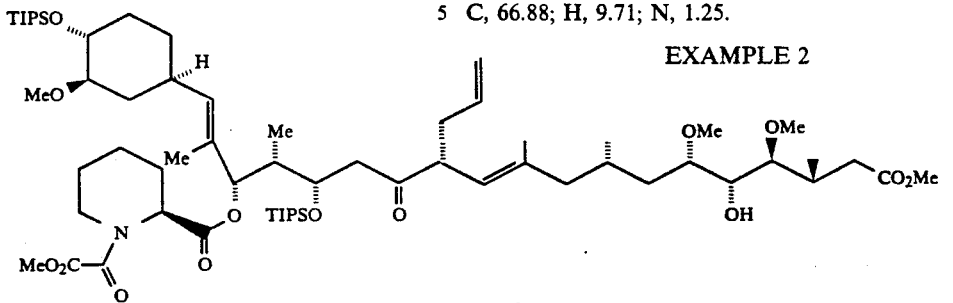

anes/ethyl acetate. (5:1) as the eluent afforded 14.04 g (99%) of 2 as a colorless foam which was characterized by $^1$H, $^{13}$C NMR, IR and MS. Anal. Calcd for $C_{62}H_{109}NO_{12}Si_2$: C, 66.685; H, 9.838; N, 1.25. Found: C, 66.88; H, 9.71; N, 1.25.

EXAMPLE 2

3

EXAMPLE 1

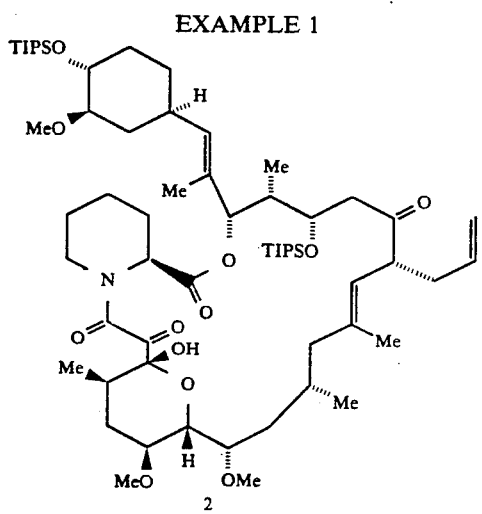

24-32-FK-506-bis-(triisopropylsilyl)-ether 2

To a 0° C. solution of FK-506 1 (10.2 g, 12.68 mmol) in 125 mL sieve dried CH$_2$Cl$_2$ was added 2,6-lutidine (7.4 mL, 63.5 mmol) and TIPSOTf (14.3 mL, 53.2 mmol). After stirring at 0° C. for 1.5 h, the yellow tinted solution was warmed to 25° C. and aged for 16 h. The mixture was then cooled to 0° C. and methanol (1.55 mL, 38.2 mmol) was added dropwise and the resulting solution was aged for 15 min. The mixture was partitioned with sat'd aqueous NaHCO$_3$ (500 mL) and CH$_2$Cl$_2$ (200 mL) and the layers were separated. The aqueous phase was reextracted with CH$_2$Cl$_2$ (2×200 mL). The combined CH$_2$Cl$_2$ phase was washed with water (200 mL), dried with MgSO$_4$ and concentrated in vacuo to afford 20 g of a yellow viscous oil. Chromatography on silica gel (325 g, 230–400 mesh) with hex- Hydroxy-ester 3

To a 25° C. solution of 24,32-FK-506-bis(triisopropylsilyl) ether 2 (23.1 g, 20.7 mmol) in 300 mL sieve dried benzene and 100 mL sieve dried methanol was added Pb(OAc)$_4$ (9.67 g, 21.8 mmol) and the resulting mixture was aged at 25° C. for 4 h. The mixture was then quenched into sat'd aqueous NaHCO$_3$ (800 mL) and extracted with ethyl acetate (3×350 mL). The combined ethyl acetate phase was washed with water (350 mL), dried with MgSO$_4$ and concentrated in vacuo to afford 22.9 g of a white gummy foam. The foam was dissolved in methanol (300 mL) at 25° C. concentrated in vacuo to remove any residual ethyl acetate. The foam was then redissolved in sieve dried methanol (350 mL) at 25° C. and anhydrous K$_2$CO$_3$ (145 mg) was added. After 2 h additional K$_2$CO$_3$ (43 mg) was added. After 5 h total reaction time at 25° C. the solution was decanted away from the solid K$_2$CO$_3$ and was concentrated in vacuo to afford 23.4 g of a yellow tinted gum. Chromatography on silica gel (1150 g, 230–400 mesh) with CH$_2$Cl$_2$/acetone (20:1) as the eluent followed by CH$_2$Cl$_2$/acetone (15:1) afforded 2.52 g (10.6%) of the valerolactone 4 as a colorless foam and 16.8 g (69%) of the desired methyl ester 3 as a colorless foam.

EXAMPLE 3

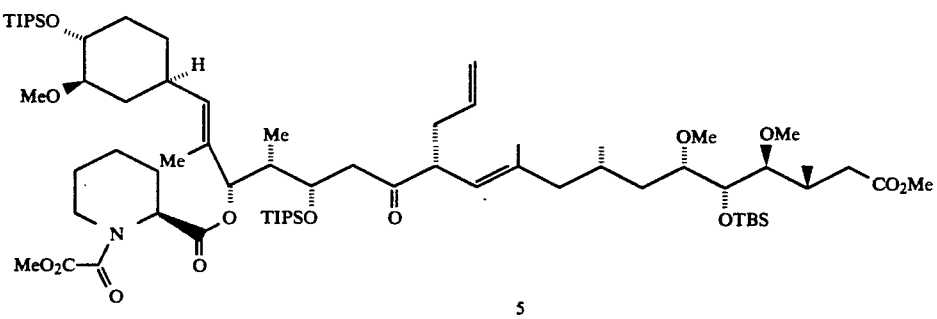

5

C.14 TBS-ether 5

To a 0° C. solution of the hydroxy-ester 3 (16.8 g, 14.25 mmol) in 210 mL dry CH$_2$Cl$_2$ was added 2,6-lutidine (3.3 mL, 28.3 mmol) and then tert-butyldimethylsilyl triflate (4.9 mL, 21.3 mmol) and the solution was stirred at 0° C. for 2 h, then it was allowed to warm to 25° C. After 1 hr at 25° C. additional tert-butyldimethylsilyl triflate (0.35 mL, 1.52 mmol) was added to the 25° C. solution. After an additional 1.5 hr age, the solution was cooled to 0° C. and sieve dried methanol (0.58 mL, 14.3 mmol) was added and the mixture was aged at 0° C. for 15 min. The mixture was partitioned with saturated aqueous NaHCO₃ (1000 mL) and extracted with CH₂Cl₂ (3×300 mL). The combined CH₂Cl₂ layer was washed with water (1×300 mL), dried with MgSO₄ and concentrated in vacuo to afford 21.4 g of a tan oil that was purified by chromatography on silica gel (1,070 g, 230–400 mesh) with hexanes/ethyl acetate (5:1) as the eluent. The TBS ether 5 (14.4 g, 78.3%) was isolated as a white gummy foam and gave satisfactory $^1$H and $^{13}$C NMR, IR and mass spectral data. Anal Calcd for $C_{70}H_{129}NO_{14}Si_3$:C. 65.02; H, 10.055; N, 1.08. Found: C, 65.18; H, 10.06; N, 1.09.

EXAMPLE 4

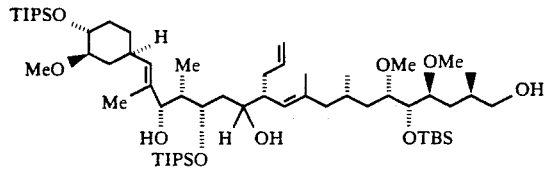

6

Triols 6 (R/S)

To a 0° C. solution of methyl ester 5 (13.3 g, 10.28 mmol) in sieve dried THF (375 mL) was added lithium aluminum hydride (1.18 g, 31.1 mmol) in several portions, and the gray suspension was aged at 0° C. for 3 h. Diethyl ether (300 mL) was added and then water was cautiously added dropwise until bubbling had stopped (several mL). The mixture was then partitioned with saturated Na₂SO₄ (400 mL) and extracted with ethyl acetate (3×400 mL). The combined ethyl acetate layer was washed with brine (400 mL), dried with MgSO₄ and concentrated in vacuo to afford 11.8 g of a brownish gummy foam. The crude foam was purified by chromatography on silica gel (580 g, 230–400 mesh) eluting with hexanes/ethyl acetate (3:1) to afford 5.9 g (65.6%) of the triols 6 as an inseparable 2.5 to 1 mixture of C.22-R/S epimers, respectively. Anal. Calcd for $C_{60}H_{120}Si_3O_9$: C, 67.36; H, 11.305. Found: C, 67.39; H, 11.38.

EXAMPLE 5

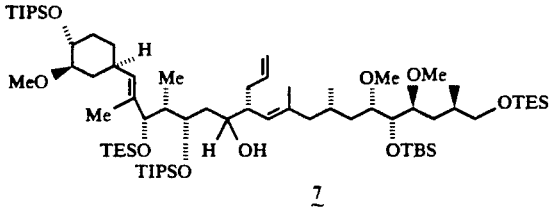

7

C.22 alcohols 7(R/S)

To a −10° C. solution of triols 6(R/S) (2.33 g, 2.18 mmol) in sieve dried pyridine (33 mL) was added TESCl (0.740 mL, 4.40 mmol) over a 5 minute period. After a 1.75 h age at −10° C., additional TESCl (0.092 mL, 0.55 mmol) was added. After an additional 1 h age, anhydrous methanol (0.088 mL, 2.17 mmol) was added and the mixture was aged at −10° C. for 0.25 hr. The mixture was partitioned with saturated aqueous NaHCO₃ (100 mL) and extracted with CH₂Cl₂ (3×100 mL). The combined CH₂Cl₂ layer was washed with saturated aqueous NaHCO₃ (100 mL), dried with MgSO₄ and concentrated in vacuo to afford 3.7 g of a tan viscous oil. The crude mixture was purified by chromatography on silica gel (175 g, 230–400 mesh) with hexanes/ethyl acetate (18:1 to 15:1) as the eluent to afford 2.726 g (96.3%) of the C.22 alcohols 7(R/S) as a colorless foam. Anal. Calcd for $C_{72}H_{148}O_9Si_5$: C, 66.605; H, 11.49. Found: C, 66.82; H, 11.77.

EXAMPLE 6

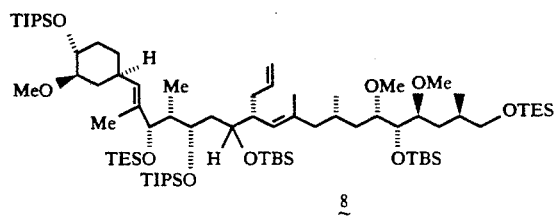

8

C.22-TBS ethers 8(R/S)

To a 0° C. solution of C.22 alcohols 7(R/S) (4.55 g, 3.50 mmol) in 100 mL sieve dried CH₂Cl₂ was added 2,6-lutidine (1.20 mL, 10.3 mmol) and then tertbutyldimethylsilyl triflate (1.60 mL, 6.97 mmol). After 0.5 h the mixture was brought to 25° C. and aged for 14 h. The mixture was cooled to 0° C. and anhydrous methanol (215 microliters, 5.30 mmol) was added and the mixture was aged for 0.5 h. The mixture was partitioned with 50% saturated aqueous NaHCO₃ (125 mL) and extracted with CH₂Cl₂ (3×125 mL). The combined CH₂Cl₂ layer was washed with water (125 mL), dried with magnesium sulfate and concentrated in vacuo to afford 5.3 g of a tan oil. The crude mixture was purified by chromatography on silica gel (260 g, 230–400 mesh) eluting with hexanes/ethyl acetate (15:1) to afford 4.86 g (98%) of the C.22 TBS ethers 8(R/S) as a gummy white foam. Anal Calcd for $C_{78}H_{162}O_9Si_6$: C, 66.32, H, 11.56. Found: C, 65.93; H, 11.77.

EXAMPLE 7

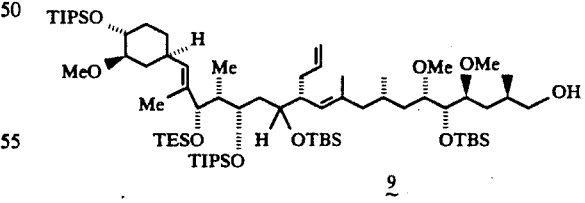

9

22(R) and 22(S)-C.10 primary alcohols 9

To a solution of bis-TES ethers 8(R/S) (4.85 g, 3.43 mmol) in 155 mL THF was added 15.5 mL water and 30 mL of acetic acid over a 10 minute period. The mixture was heated to 40° C. and aged for 12 h, then at 50° C. for 2.5 hr. The mixture was cooled to 0° C. and poured slowly into a solution/suspension of 72 g NaHCO₃ in 450 mL H₂O. The mixture was then extracted with ethyl acetate (3×450 mL) and the combined ethyl acetate layer was washed with saturated aqueous NaHCO₃ (115 mL), brine (115 mL) and dried with magnesium sulfate. The volatiles were removed in vacuo to afford 5.01 g of a tan gum that was purified by silica gel chromatography (675 g, 230–400 mesh). Gradient elution with hexanes/ethyl acetate (8:1 to 2:1) afforded 742 mg (16.6%) of pure less polar 22(S)-C.10 primary alcohol 9(S), 305 mg (6.8%) of mixed fractions and 2.315 g (52%) of the 22 R)-C.10 primary alcohol 9(R) which had $^1$H and $^{13}$C NMR, IR and MS data consistent with the structure. Anal. Calcd for $C_{72}H_{148}O_9Si_5$: C, 66.605; H, 11.489. Found: C, 66.47; H, 11.73.

EXAMPLE 8

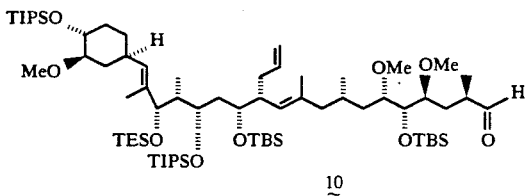

Aldehyde 10

To a −78° C. solution of oxalyl chloride (148 microliters, 1.70 mmol) in 10 mL sieve dried $CH_2Cl_2$ was added a solution of dimethyl sulfoxide (200 @1, 2.82 mmol) in 4 mL $CH_2Cl_2$ over a period of 5 min and the resulting mixture was aged at −78° C. for 0.5 h. A solution of the primary alcohol 9(R) (1.06 g, 0.816 mmol) in 10 mL $CH_2Cl_2$ was added to the −78° C. chlorosulfonium salt solution followed by a 5 mL $CH_2Cl_2$ flush. The resulting white slurry was aged at −78° C. for 1.5 h, then triethylamine (983 microliters, 7.05 mmol) was added and the solution warmed to −40° C. and aged at −40° C. for 1 h. Aqueous NaHSO₄ (0.5 M, 75 ml) was added at −40° C. and the mixture was extracted with hexanes (4×100 mL). The combined hexane layer was washed with water (1×50 ml), dried with MgSO₄ and concentrated in vacuo to afford 1.05 g of crude material that was chromatographed on silica gel (90 g, 230–400 mesh). Elution with hexanes/ethyl acetate (15:1) gave 977 mg (95.8%) of the aldehyde 10 as a white foam. Aldehyde 10 gave $^1$H and $^{13}$C NMR, IR and MS data in accord with its structure.

EXAMPLE 9

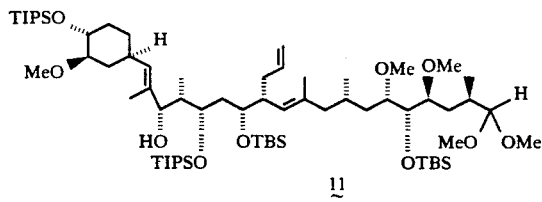

Dimethyl acetal II

To a solution of aldehyde 10 (2.07 g, 1.60 mmol) at 0° C. in 105 mL sieve dried THF was added methanol (155 mL), trimethylorthoformate (3.13 mL, 28.6 mmol) and pyridinium para-toluenesulfonate (555 mg, 2.2 mmol) and the mixture was warmed to 18° C. After 2 h, 444 mg of pyridinium para-toluenesulfonate was added, and the mixture was warmed to 25° C. After 3 h at 25° C., pyridine (4.9 mL, 60.5 mmol) was added with ice bath cooling and the mixture was poured into 250 mL saturated aqueous NaHCO₃ and extracted with $CH_2Cl_2$ (3×200 mL). The combined $CH_2Cl_2$ layer was washed with 50% aqueous NaHCO₃ 120 mL), dried with MgSO₄ and concentrated in vacuo. The resulting crude oil was chromatographed on 200 g SiO₂ (230–400 mesh) eluting with hexanes/ethyl acetate ((15:1), 1.6 L; (8:1), 850 mL; (3:1), flush) to afford 1.637 g (83.5%) of the dimethyl acetal 11 as a colorless oil, which exhibited $^1$H and $^{13}$C NMR, IR and MS consistent with its structure. Anal. Calcd for $C_{68}H_{138}O_{10}Si_4$: C, 66.501; H, 11.325. Found: C, 66.43;, H, 11.68.

EXAMPLE 10

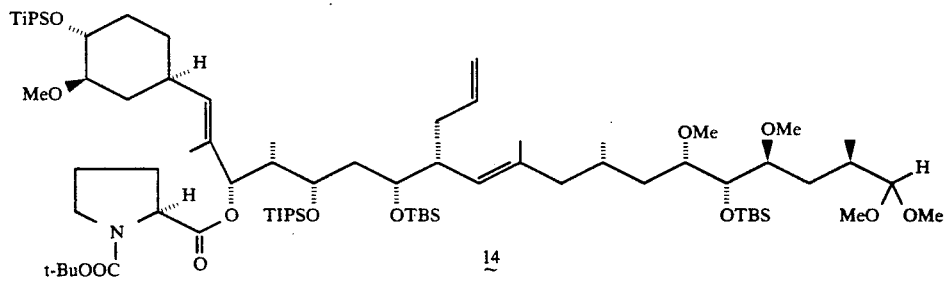

N-BOC proline ester 14

To a solution of C.26 alcohol 11 (388.5 mg, 0.316 mmol) in 6 mL dry $CH_2Cl_2$ at 50° C. was added solid N-Boc-(L)-proline 273 mg, 1.27 mmol) then 1,3-dicyclohexylcarbodiimide (DCC, 262 mg, 1.27 mmol) and N,N-dimethylaminopyridine (DMAP, 7.8 mg, 0.064 mmol) and the resulting solution was aged at −50° C. for 1.5 h. The mixture was warmed to −19° C. and aged for 30 h, then N-BOC-(L)-proline (136 mg), 131 mg DCC and 4 mg DMAP were added and the slurry was aged again for 24 h. The slurry was then warmed to 25° C., filtered to remove the precipitate and the filter cake was washed with hexanes/ethyl acetate (6:1). The volatiles were removed in vacuo to afford 970 mg of a crude oil that was purified by silica gel chromatography (95 g, 230–400 mesh). Elution with hexanes:ethyl acetate (3:1) gave 435.8 mg (96.7%) of the N-BOC proline ester 14. The ester 14 exhibited $^1$H and $^{13}$C NMR, IR and MS data in accord with its structure. Anal. Calc'd for $C_{78}H_{153}Si_4O_{13}N$: C, 65.726; H, 10.819; N, 0.983. Found: C, 65.89; H, 11.10; N, 1.00. The material had a rotation $[\alpha]D^{25} = -42.73°$ in methylene chloride at c=1.16 g/100 ml.

Subjecting 14 to the following synthetic steps, as also outlined in companion copending case Ser. No. 07/375,091, filed Jun. 30, 1989, will result in regenerating the FK-macrolide, specifically, for example, the immunosuppressant FK-525.

EXAMPLE 11

2R,4S,5R,6S,8S,12R,13R,15S,16R,17S,1'R,3'R-4'R-)-E,E-4,6-dimethoxy-2,8,10,16,18-pentamethyl-5,13-bis-t-butyldimethylsilyloxy-12-(prop-2'-en-1'-yl)-15-triisopropylsilyloxy-17-((N-t-butyl-carboyloxy-L-prolinoyl)-19-(3'-methoxy-4'-triisopropylsilyoxycyclohexyl)-nonadecan-10,18-dienal, 15

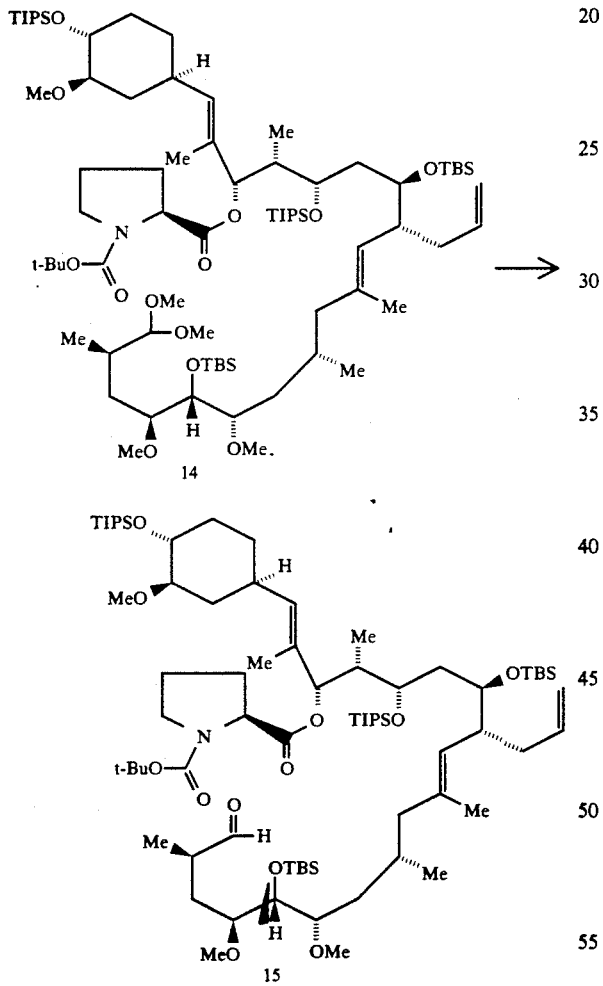

Dimethyl acetal 14 (427 mg, 0.299 mmol) was dissolved in 13 ml of methylene chloride under a nitrogen atmosphere and glyoxylic acid monohydrate (276 mg, 3 mmol) and acetic acid (171 microliters, 10 equiv) were added. The resulting solution was stirred at 40° C. for 2.5 hr. The mixture was cooled to 25° C. and poured into 25 ml of saturated sodium bicarbonate solution at 0° C. The phases were separated and the aqueous phase was extracted with 3×75 ml of methylene chloride. The organic phases were combined, dried over sodium sulfate, and concentrated in vacuo. The resulting material was purified by column chromatography on 50 g of silica gel eluting with hexanes:ethyl acetate (7:1) to give the desired aldehyde 15 (390 mg, 95%). The material was homogeneous by both $^1H$ and $^{13}C$ NMR.

EXAMPLE 12

Preparation of 2-P-Methoxybenzyl-Acetic Acid Phenyl Alanine Derived Oxazolidinone Imide. 19

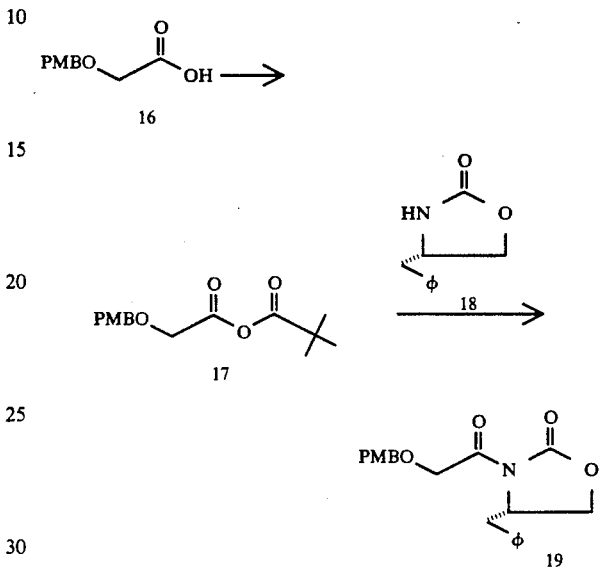

A. Preparation of 16 p-Methoxybenzyl alcohol (83.1 g) was dissolved in 75 ml of toluene and added dropwise (under a nitrogen atmosphere) over a period of 30 min. to suspension of sodium hydride (53 g of a 60% oil dispersion, 2.20 equivalents) in 300 ml of toluene. The internal temperature rose from 24° C. to 35° C. during the addition. After hydrogen evolution had ceased (ca. 20 min.), 2-bromoacetic acid (in 400 ml of toluene) was added over 1 hour dropwise under a nitrogen atmosphere keeping the internal temperature below or equal to 40° C. The addition of 2-bromoacetic acid was highly exothermic and external cooling was necessary. After 45 min., the mixture was diluted with 400 ml of toluene and heated at 95° C. for 2 hr. The mixture was cooled to 25° C. and quenched by the addition of 400 ml of water and the layers were separated. The aqueous phase was extracted with 2×200 ml of methyl-t-butyl ether. The aqueous layer was acidified with 60 ml of 1N $H_2SO_4$ and extracted with 3×400 ml of ethyl acetate. The combined organic phases were concentrated in vacuo to a yellow solid 16 (mp 49°-53° C., 103 g, 87% yield).

B. Preparation of 17. 19

2-p-Methoxybenzyl acetic acid 16 (3.92 g, 0.02 mol) was dissolved in 100 ml of ether and cooled to −78° C. under a nitrogen atmosphere. Triethylamine was added (2.86 ml, 0.0205 mol) followed by Pivaloyl chloride (2.52 ml, 0.0205 mol). The mixture was warmed to 0° C. over 30 min. and then stirred at 0° C. for 2 hr. to give mixed anhydride 17. The solution was then cooled to −78° C. (SOLUTION A).

In a separate flask the (S) phenylalanine derived oxazolidinone 18 (3.45 g, 0.0195 mol) was dissolved in 30 ml of tetrahydrofuran and cooled to −78° C. under a nitrogen atmosphere. n-Butyllithium (14.3 ml of a 1.36 M solution in hexane) was added via cannula, and then was stirred for 15 min. at −78° C. (SOLUTION B).

Solution B was then added, via cannula, to solution A at −78° C. The resulting mixture was stirred 15 min. at −78° C., warmed to 0° C. over 30 min., and then stirred for 1 hour at 0° C. Sixty ml of water was then added and the mixture was extracted with 3×50 ml of methylene chloride. The combined organic extracts were washed with 50 ml of saturated sodium bicarbonate solution and 50 ml of saturated sodium chloride solution and were dried over sodium sulfate. Concentration in vacuo and flash chromatography with silica gel (elution with 3:1, hexanes:ethyl acetate) gave the desired p-methoxybenzyl acetate derived oxazolidinone imide 19 (5.51 g).

EXAMPLE 13

2S,3R,4R,6S,7R,8S,10S,14R,15S,17S,18R,19S,1′R,3′R-'R)-E,E-2-(p-Methoxybenzyloxy)-3-hvdroxy-4,10,12-18,20-pentamethyl-6,8-dimethoxy-7,15-bis-t-butyldimethylsilyloxy-14-(prop-2′-en-1′-yl -17-triisopropylsilyloxy-19-((N-t-butylcarboyloxy-L-prolinoyloxy)-21-(3′-methoxy-4′-triisopropylsilyoxycyclohexyl)-12,20-dienoic acid derived oxozolidin-2′-one imide 20 were added and the mixture was stirred for 1.5 hr. Aldehyde 15 (361 mg, 0 262 mmol) in 3.6 ml of toluene was added and the mixture was stirred for 1.0 hr at −50° C. The mixture was warmed to −30° C. and stirred for an additional 1.5 hr. Tlc analysis (3:1, hexanes:ethyl acetate) showed the reaction to be complete at this time. The reaction mixture was quenched by the addition of 8.0 ml of saturated sodium bicarbonate solution and then partitioned between 40 ml of aqueous sodium bicarbonate solutions and 75 ml of ethyl acetate. The layers were separated and the aqueous phase was extracted with 2×75 ml of ethyl acetate. The combined organic layers were washed with 20 ml of saturated sodium chloride solution and dried over sodium sulfate.

Concentration in vacuo gave 0.805 g of a crude oil. The product was purified by column chromatography on 70 g of silica gel eluting with hexanes:ethyl acetate (3:1) to give imide 20 (0.385 g, 85%). The material was homogeneous by $^1$H and $^{13}$C NMR.

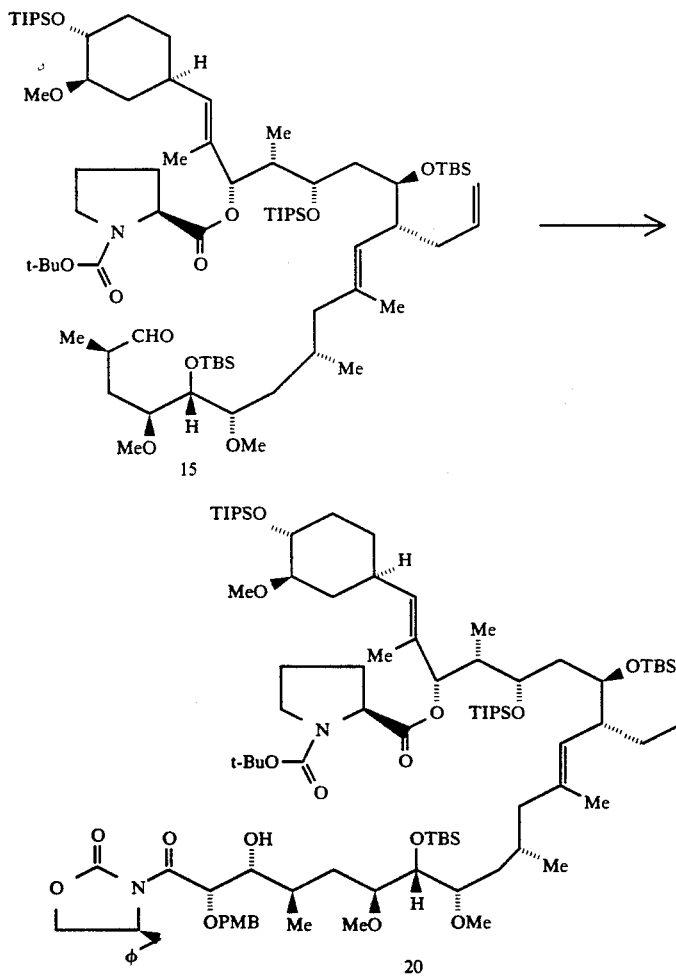

p-Methoxybenzylacetimide 19 (286 mg, 3.0% equiv. was dissolved in 6.3 ml of anhydrous toluene at −50° C. under a nitrogen atmosphere. Triethylamine (0.150 mL, 4.0 equiv) and dibutylboron triflate (0.195 ml, 2.9 equiv)

EXAMPLE 14

(2S,3R,4R,6S,7R,8S,10S,14R,15S,17S,18R,19S,1'R,-3'R-4'R)-E,E-2-(4'methoxybenzyloxy)-3-hydroxy-4,10,12-18,20-pentamethyl-6,8-dimethoxy-7,15-bis-t-butyldimethylsilyloxy-14-(prop-2'-en-1-yl)-17-triisopropylsilyloxy-19-(N-t-butylcarboyloxy-L-prolinoyloxy)-21-(3'-methoxy-4'-triisopropylsilyoxycyclohexyl)-12,20-dienoic acid, 21 tion of 7.3 ml of 10% aqueous sodium bisulfate solution. The mixture was diluted with 20 ml of hexanes and the pH was adjusted to 3.0–3.5 with 0.5 N sodium bisulfate solution. The mixture was extracted with 3×50 ml of hexanes and the combined organic layers were washed with 20 ml of water and dried over sodium sulfate. Concentration in vacuo gave 1.081 g, quantitative yield, of the desired carboxylic acid 21.

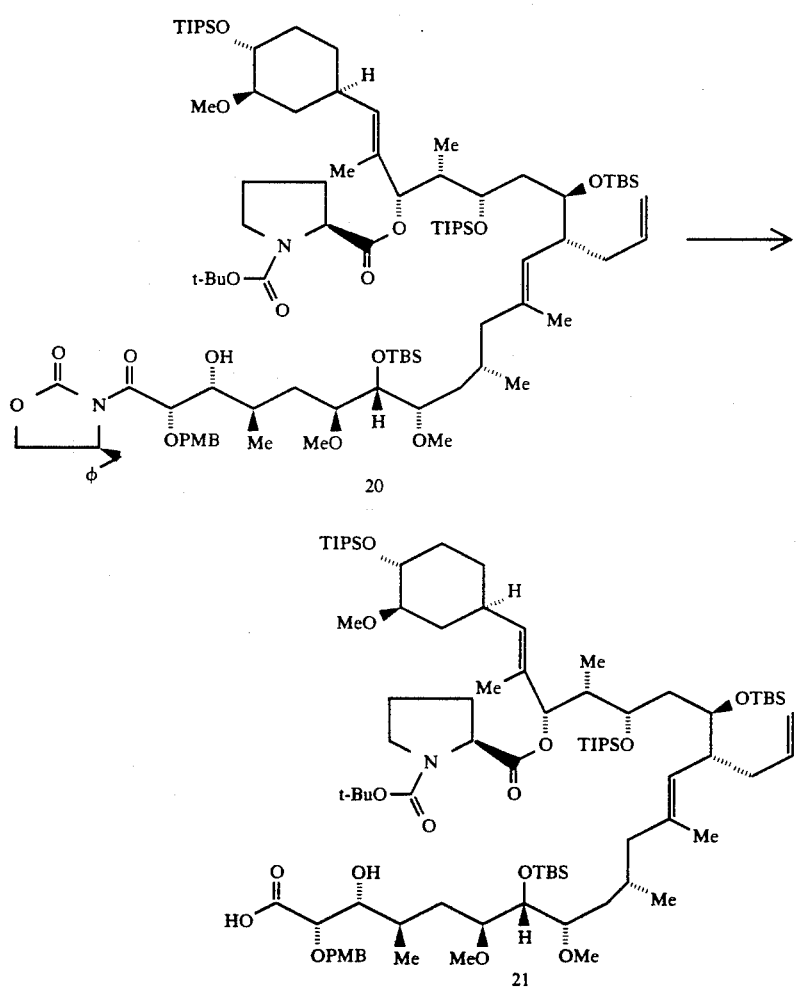

Imide 20 (1.191 g) was dissolved in 6.0 ml of tetrahydrofuran and 1.35 ml of water and cooled to 0° C. Aqueous 30% hydrogen peroxide solution (0.560 ml, 8 equiv) and lithium hydroxide monohydrate (58 mg, 1.38 mmol) were added. The mixture was stirred at 0° C. for 1.5 hr. and then concentrated in vacuo to remove the tetrahydrofuran. The reaction was quenched at 0° C. by addi-

EXAMPLE 15

(2S,3R,4R,6S,7R,8S,10S,14R,15S,17S,18R,19S,1'R,3'-R,-4'R)E,E-2-(4'methoxybenzyloxy)-3-triethylsilyl oxy4,10,12,18,20-pentamethyl-6,8-dimethoxy-7,15-bis-t-butyldimethylsilyloxy-14-(prop-2'-en-1'-yl)-17-triisopropylsilyloxy-19-(L-prolinoyloxy)-21-(3'-methoxy-4'-triisopropylsilyoxycyclohexyl)-12,20-dienoic acid, 22 tained at 15° C. or less). The concentrate was then dissolved in methylene chloride and passed through a column containing 83.5 g of silica gel. Column elution was with 700 ml of methylene chloride; 930 ml of 1% methanol/methylene chloride; 700 ml 4% methanol/methylene chloride; and 1000 ml 8% methanol methylene chloride. The column rich cuts were combined and concentrated to give 154 mg of the amino acid 22

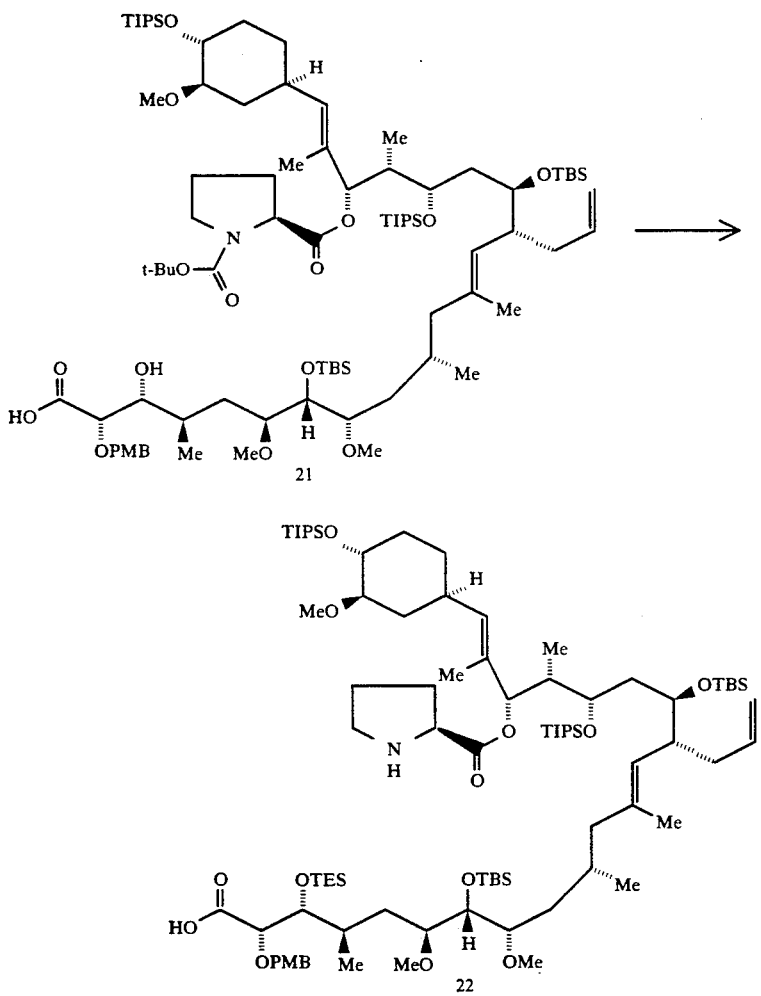

Acid 21 (200 mg) was dissolved in 7.0 ml of methylene chloride at 0° C. and 2,6-lutidine (6.0 equiv) was added. Triethylsilyltriflate (5.5 equiv) was added and the mixture was stirred at −20° C. for 30 minutes. The reaction mixture was diluted with 5 ml of distilled water and extracted with 3×25 ml of hexane. The hexane portions were combined, dried over sodium sulfate and concentrated in vacuo (bath temperature was maintained (76%).

EXAMPLE 16

C.9-(p-Methoxybenzyloxy)-C.10-triethylsilyloxy-C.14,
C.22-bis-t-butyldimethylsilyloxy-C.24.
C.32-bis-triisopropylsilyloxy-hexahydro-FK-525
(FK-numbering system) 23

EXAMPLE 17

C.9
C.10-Dihydroxy-C.14.C.22-bis-t-butyldimethylsilyloxy-
C.24.C.32-bis-(triisopropylsilyloxy)-FK-525, 24

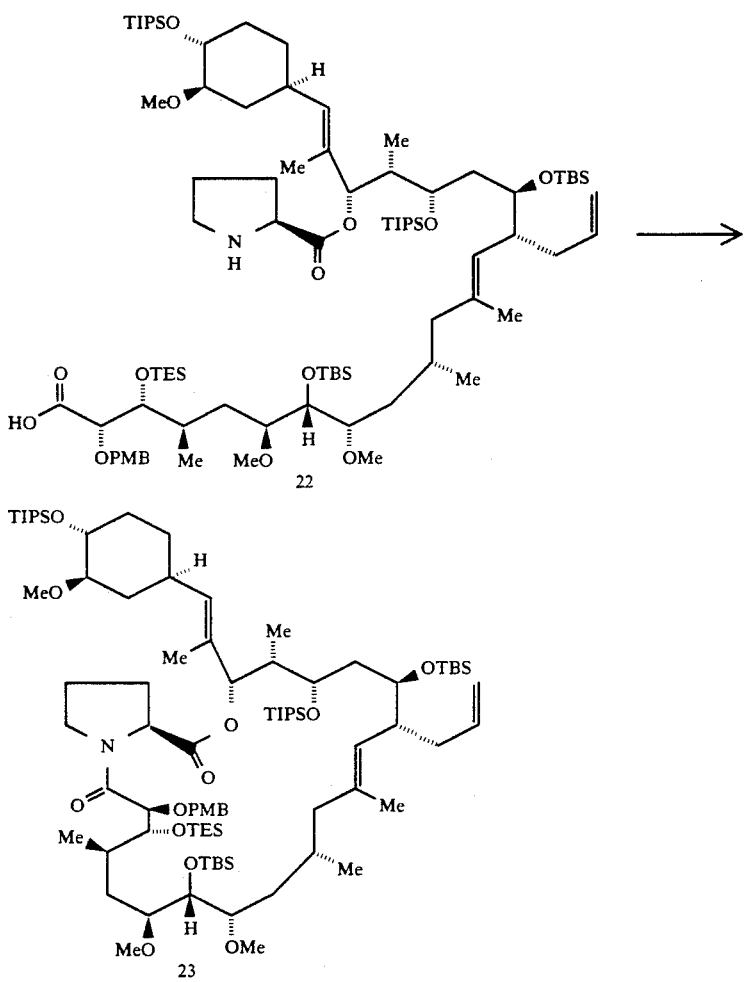

2-Chloro-N-methylpyridinium iodide (60 mg, 2.0 equiv) was dissolved in 150 ml of methylene chloride under a nitrogen atmosphere and triethylamine (0.078 mL, 5 equiv) was added. Amino acid 22 (186.5 mg) in 15 ml of anhydrous methylene chloride containing 0.046 ml of triethylamine was added via syringe over a period of 1.5 hr at 25° C. The mixture was stirred at 25° C. for 13 hr. and then diluted with 20 ml of water. The layers were separated and the aqueous layer was extracted with 2×25 ml of methylene chloride. The organic portions were combined dried over sodium sulfate and concentrated in vacuo to give an oil. The crude oil was purified by column chromatography on silica gel (38 g, elution with hexanes/ethyl acetate 15:1). The rich cuts were combined and concentrated to give the desired macrocycle 23 (130 mg, 70% yield). Macrocycle 23 was characterized by $^1$H and $^{13}$C NMR.

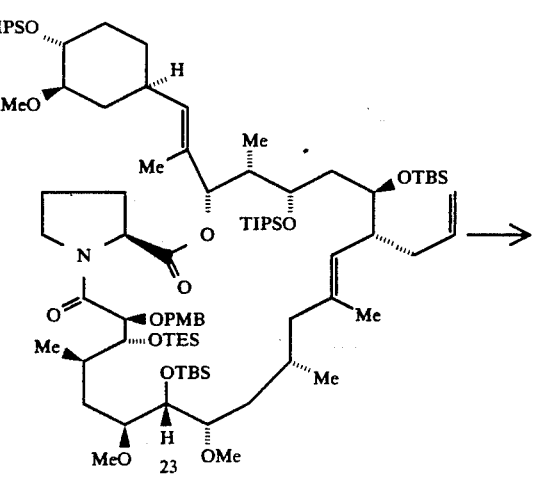

-continued

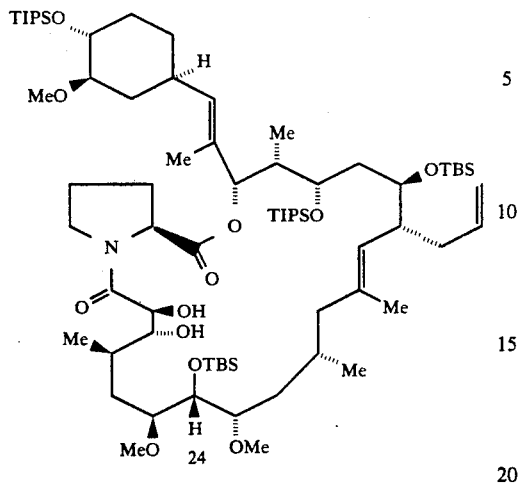

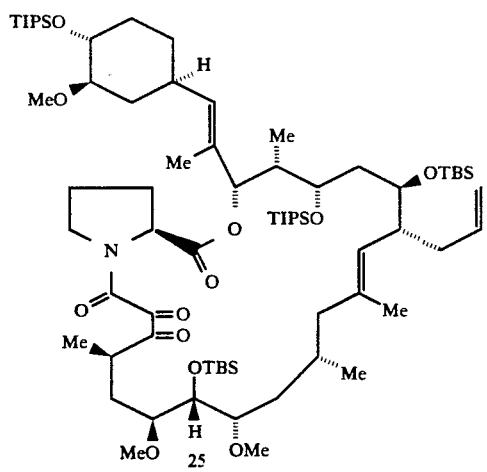

Macrocycle 23 (526 mg, 0.335 mmol) was dissolved in 3 ml of methylene chloride containing 0.18 ml of water and the mixture was stirred at 25° C. 2,3-dichloro-5,6-dicyano-1,4-benzoquinone (380 mg, 1.6 mmol) was added and the mixture was stirred at 25° C. for 5 hr. The crude mixture was then chromatographed on 42 g of silica gel (400 mesh, eluting with 200 ml methylene chloride; 320 ml 15:1 hexanes/ethyl acetate; 280 ml 6:1 hexanes/ethyl acetate). The rich cuts were combined and concentrated in vacuo to give the alcohol which was dissolved in 5.3 ml of tetrahydrofuran containing 0.6 ml of water and 0.086 ml of trifluoracetic acid. The mixture was then stirred at 25° C. for 3.5 hr. The mixture was diluted with 10 ml of saturated sodium bicarbonate solution and extracted with 3×25 ml of ethyl acetate. The combined organic phases were dried over sodium sulfate, concentrated in vacuo, and chromatographed on silica gel) elution with 6:1 hexanes:ethyl acetate) to give 358 mg of diol 24 (80% yield). Microanalysis calcd for $C_{73}H_{141}N_{12}Si_4$: C, 65.567; H, 10.627; N, 1.047 Found C, 65.67; H, 10.43; N=1.05. Rotation $[\alpha]^{25}=56.5°$, C=1.73 in methylene chloride.

EXAMPLE 18

C.14, C.22-bis-t-butyldimethylsilyloxy-C.24, C.32-bis-(triisopropylsilyloxy)-FK-525, 25

Oxalyl chloride (0.177 ml, 12 equivalents) was dissolved in 1.9 ml of methylene chloride and cooled to −78° C. under nitrogen. Dimethyl sulfoxide (0.240 ml, 20 equiv) was added and the mixture was stirred for 20 minutes. The dihydroxy macrocycle 24 (216 mg) dissolved in 2.0 ml of methylene chloride was added to the oxidant solution and the mixture was stirred at −78° C. for 3 hr. Triethylamine (1.18 ml, 50 equiv) was added and the mixture was warmed to −30° C. and stirred for 1 hr. The reaction was quenched by the addition of 30 ml of 0.5 N sodium bisulfate solution and the mixture was extracted with 3×25 ml of ethyl acetate. The ethyl acetate phases were combined, dried over sodium sulfate, concentrated in vacuo and purified by chromatography on silica gel (eluting with 70 ml 8:1 hexanes/ethyl acetate: 70 ml 6:1 hexanes/ethyl acetate) to give the desired diketo macrocycle 25 as an oil. The product was resubjected to the above reaction conditions to give 176 mg overall the desired diketone 25 (77% overall yield). The diketo macrocycle 25 was homogeneous by both $^1H$ and $^{13}C$ NMR.

EXAMPLE 19

C.22-dihydro-FK-525, 26

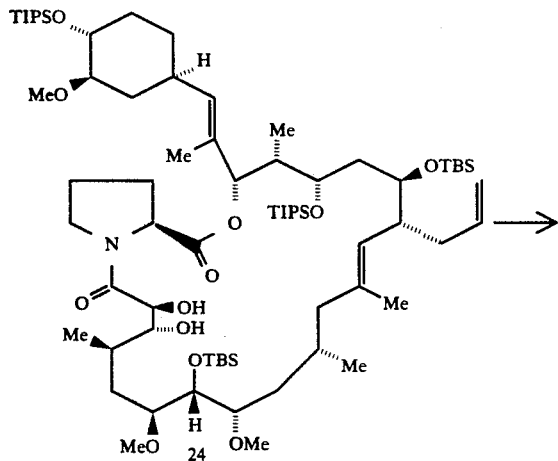

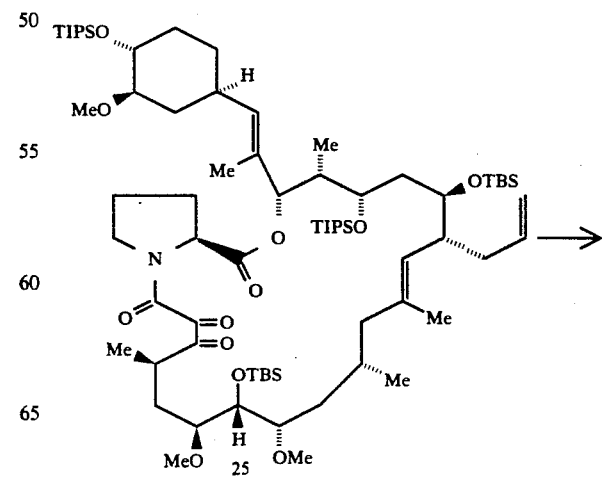

-continued

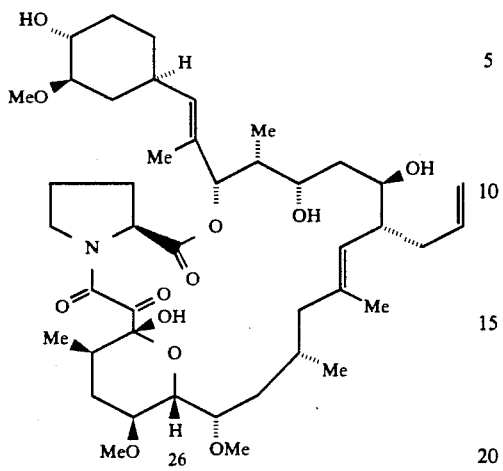

26

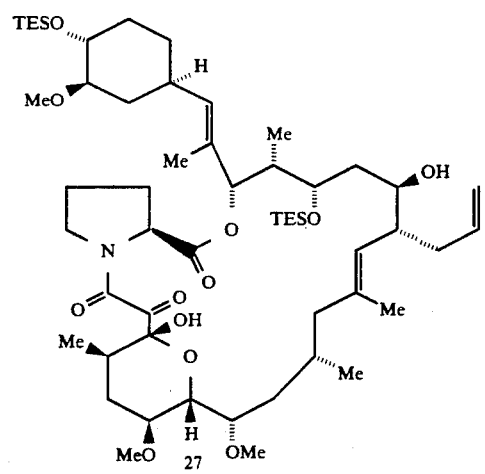

27

Diketo-macrocycle 25 (144.7 mg, 0.108 mmol) was dissolved in 7 ml of acetonitrile at 0° C. and 7 drops of 50% aqueous hydrofluoric acid was added. The mixture was stirred at 0° C. for 8 hr. and then diluted with 18 ml of saturated aqueous sodium bicarbonate solution. The mixture was extracted with 4×20 ml of ethyl aceteate and the organic layers were combined, dried over sodium sulfate, and concentrated in vacuo to an oil (102 mg). The oil was purified by chromatography on silica gel (10 g, elution with 100 ml 1:2 hexanes/ethyl acetate and then 100 ml of ethyl acetate) to give 66 mg of compound 26 (77%). The material was homogeneous by $^1$H and $^{13}$C NMR Rotation $[\alpha]$D C=−29.95°, C=0.661 in chloroform, IR 3600, 3550–3200, 1745, 1735 and 1630 cm$^{-1}$.

EXAMPLE 20

C.24.C.32-bis-triethylsilyloxy-dihydro-FK-525, 27

Analog 26 (8.9 mg) was dissolved in anhydrous pyridine at 0° C. under a nitrogen atmosphere and triethylsilylchloride (0.008 ml, 4.2 equivalents) was added. The mixture was stirred for 12 hr at 0° and then diluted with 5 ml of saturated sodium bisulfate solution. The mixture was extracted with 3×5 ml of ethyl acetate, the organic phases were combined, dried over sodium sulfate, and concentrated in vacuo. Chromatography of the residual oil on silica gel (elution with 60 nml 5:1 hexanes/ethyl acetate; 50 ml of 4:1 hexanes/ethyl acetate; 80 ml of 3:1 hexanes/ethyl acetate) to give the bis-triethylsilyloxy compound 27 (10.2 mg). The material was characterized by $^1$H and $^{13}$C NMR.

EXAMPLE 21

C.24,C.32-bis-triethylsilyloxy-dihydro-FK-525, 28

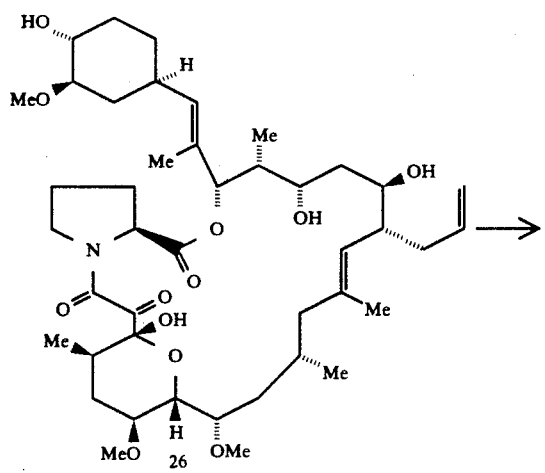

26

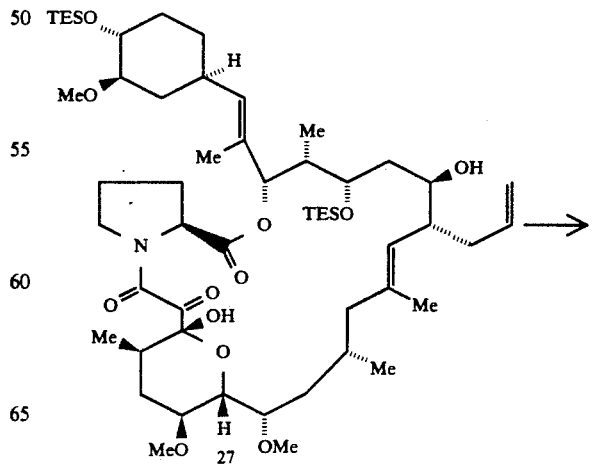

27

-continued

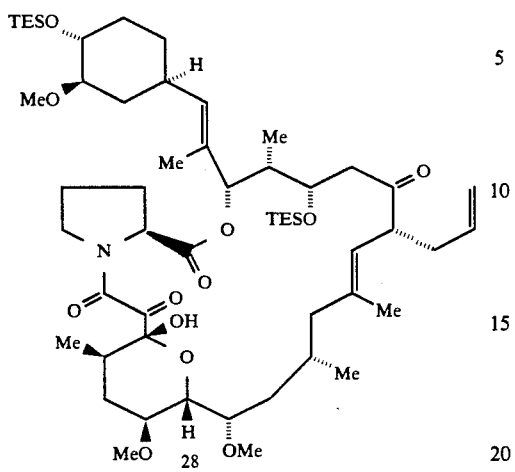

The C.22 alcohol 27 (39.5 mg) was dissolved in 2.0 ml of CH$_2$Cl$_2$ under nitrogen and pyridine (0.010 ml, 3 equiv) was added followed by Dess-Martin perioindane (27 mg, 1.5 equiv). The reaction mixture was aged for 1.5 hours at 25° C. Thin layer chromatography (hexanes:ethyl acetate 2/1) showed the absence of starting material at this time. The mixture was partitioned between 5 ml of methylene chloride and 10 ml of saturated sodium sulfate, and concentrated in vacuo to give 50 mg of a crude oil. The oil was purified by chromatography on silica gel (10 g, elution with 3:1 hexanes/ethyl acetate) to give 32.1 mg (81% yield) of the desired bis-triethylsilyl FK-525 ketone 28. This material was homogeneous by both $^1$H and $^{13}$C NMR.

EXAMPLE 22

FK-525, 29

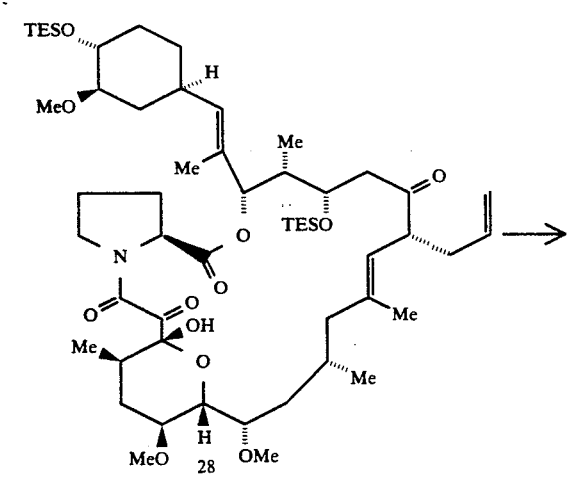

-continued

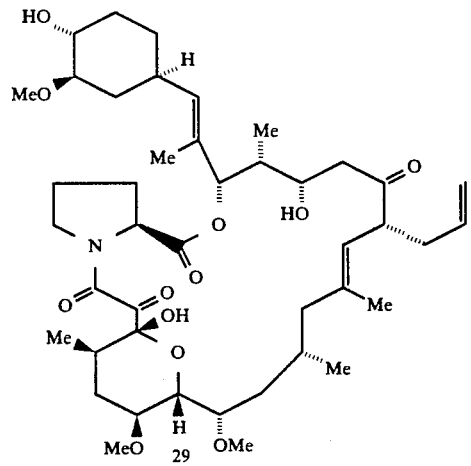

The silyl derivative 28 (32 mg) was dissolved in 2.0 ml of acetonitrile and cooled to 0° C. One drop of 50% aqueous hydrofluoric acid was added and the mixture was aged at 0° C. for 1 hr. The mixture was diluted with 5 ml of saturated aqueous sodium bicarbonate solution and extracted with 5×20 ml of ethyl acetate. The organic phases were combined, washed with 10 ml of saturated sodium chloride solution, dried over sodium sulfate, and concentrated in vacuo to give 14.2 mg of crude product. This material was purified by chromatography on silica gel (5 g, elution with 50 ml of 1:2 hexanes/ethyl acetate and then 50 ml of ethyl acetate) to give 22.2 mg of the FK-525 29 (89% yield).

IR (CHCl$_3$): $\lambda_{max}$3600, 3500-3200(vb), 1745, 1735, 1695, 1630 cm$^{-1}$.

$^{13}$C NMR (CDCl$_3$, 32 mg/mL, major rotamer only, 75.5 MHz): δ213.1, 187.9, 168.8, 162.5, 140.4, 135.4, 132.1, 129.8, 122.1, 116.6, 99.0, 84.1, 78.4, 76.5, 73.6, 73.5, 71.2, 69.0, 59.9, 57.7, 56.5, 56.2, 53.2, 48.8, 48.5, 44.0, 41.0, 36.1, 35.4, 34.8, 34.7, 32.9, 32.6, 31.1, 30.6, 28.4, 25.7, 25.4, 18.7, 16.1, 15.6, 14.0, 9.6.

[α]$^{25}$ = −98.5, C=0.195, CHCl$_3$.

What is claimed:

1. A compound of the formula:

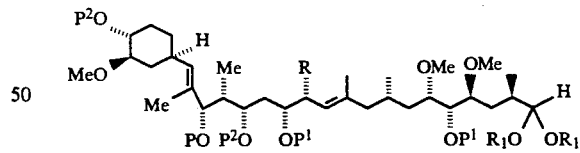

wherein P/P$^1$/P$^2$ are independently defined as H or tri(hydrocarbo)silyl, wherein said hydrocarbo groups are independently chosen from C$_1$-C$_4$ linear or branched alkyl, phenyl or benzyl, such that P can be selectively removed in the presence of P$^1$/P$^2$ and R is selected from allyl, propyl, ethyl or methyl, and R$_1$ is methyl or ethyl.

2. The compound of claim 1 wherein P$^2$ is selected from triisopropylsilyl, triphenylsilyl, tribenzylsilyl; P$^1$ is selected from isopropyldimethylsilyl, t-butyldimethylsilyl, phenyldimethylsilyl, benzyldimethylsilyl, diethylisopropylsilyl; P is selected from trimethylsilyl, triethylsilyl.

3. The compound of claim 1 wherein P$^2$ is triisopropylsilyl.

4. The compound of claim 1 wherein P¹ is t-butyldimethylsilyl.
5. The compound of claim 1 wherein P is triethylsilyl.
6. The compound of claim 1 wherein R is allyl.
7. The compound of claim 1 wherein R is ethyl.
8. The compound of claim 1 wherein R is methyl.
9. A compound of the formula:

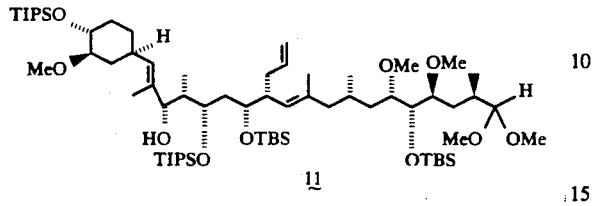

11

10. A process for degrading an FK-506 type macrolide to a useful intermediate therefor comprising the step of

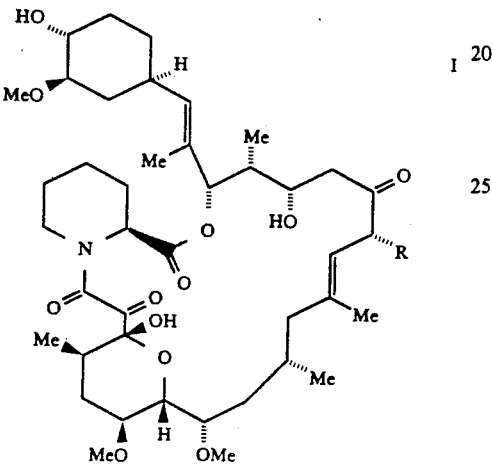

a) contacting I, where R¹ is selected from allyl, methyl, ethyl or propyl, with a silylating agent in the presence of an amine hydrogen acceptor to form II;

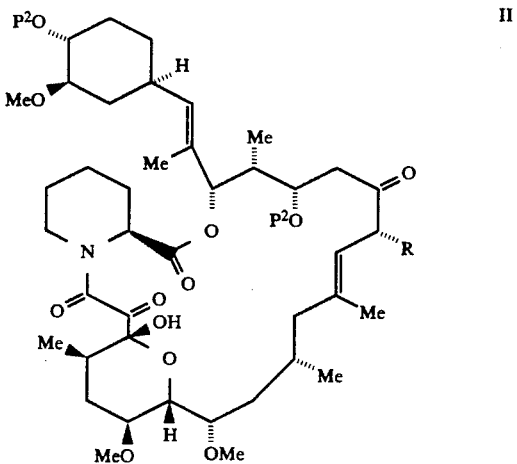

b) contacting II with Pb(OAc)$_4$ in a dry inert organic solvent at a temperature in the range of 10°–40° C. followed by methanolic K$_2$CO$_3$ to form III;

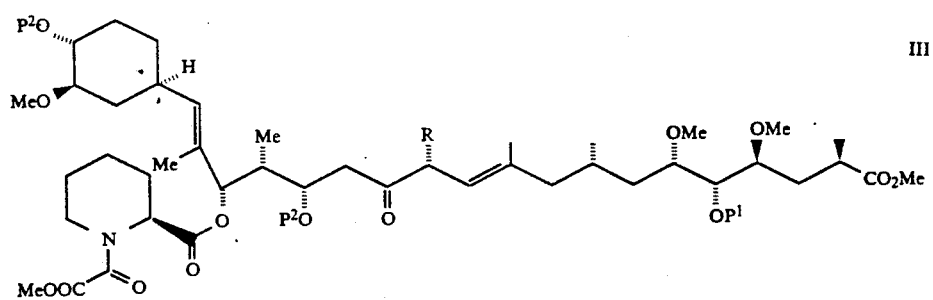

c) contacting III with a silylating agent at 0°–10° C. in the presence of an organic amine hydrogen acceptor to form V;

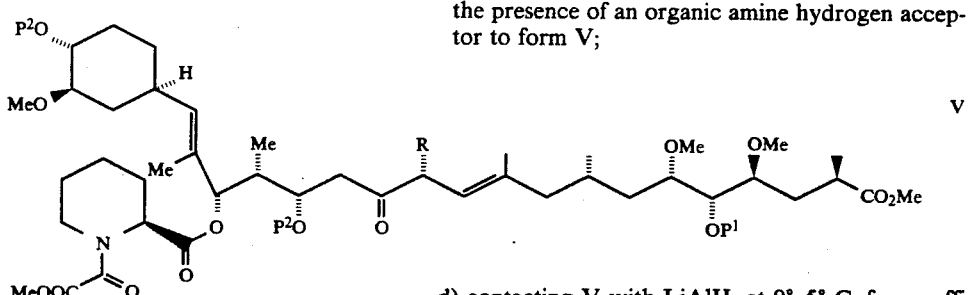

d) contacting V with LiAlH$_4$ at 0°–5° C. for a sufficient time to form the triols VI (R/S);

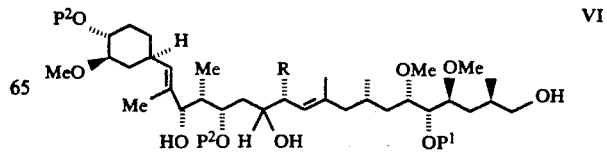

e) contacting the triols VI (R/S) with silylating agent at −10° C. to 0° C. for a sufficient time to form the alcohol VII (R/S);

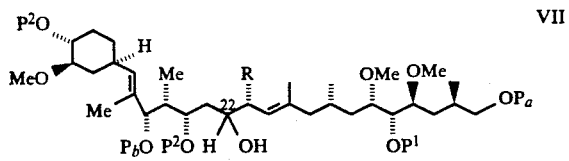

f) contacting alcohol VII (R/S) with silylating agent in the presence of an organic amine hydrogen acceptor at a temperature in the range of 0°–10° C. for a sufficient time to form the ether VIII (R/S);

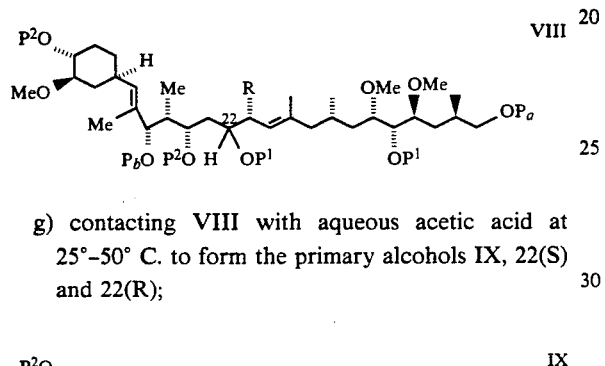

g) contacting VIII with aqueous acetic acid at 25°–50° C. to form the primary alcohols IX, 22(S) and 22(R);

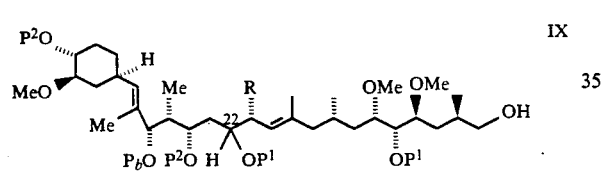

h) contacting IX with oxalyl chloride, DMSO and an organic amine at a temperature in the range of about −80° to −60° C. or CrO$_3$-pyridine at 25° C. in a dry inert organic solvent for a sufficient time to form X;

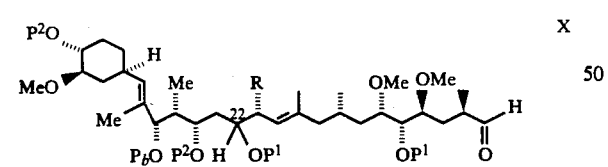

i) contacting X with methanol, trialkylorothoformate and pyridinium p-toluenesulfonate at 0°–10° C. in a dry organic solvent for a sufficient time to form XI;

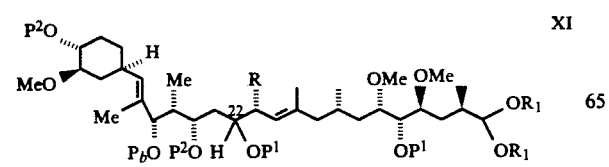

wherein P/P$^1$/P$^2$ are independently defined as H or tri(hydrocarbo)silyl, and P$_a$ and P$_b$ are either H or P, and wherein said hydrocarbo groups are independently chosen from C$_1$–C$_4$ linear or branched alkyl, phenyl or benzyl, such that P can be selectively removed in the presence of P$^1$, P$^2$, or both, and R$_1$ is methyl or ethyl.

11. The process of claim 10 wherein R is allyl or ethyl, and R$_1$ is methyl.

12. The process of claim 10 wherein P$^2$ is triisopropylsilyl, P$^1$ is t-butyldimethylsilyl and P is trimethylsilyl.

13. A process for degrading FK-506 to a useful intermediate therefor comprising the step of

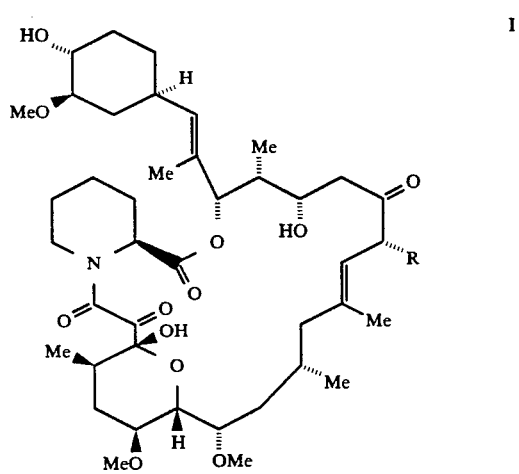

a) contacting I, where R is selected from allyl, methyl, ethyl or propyl, with TIPS triflate in the presence of an amine hydrogen acceptor to form 2;

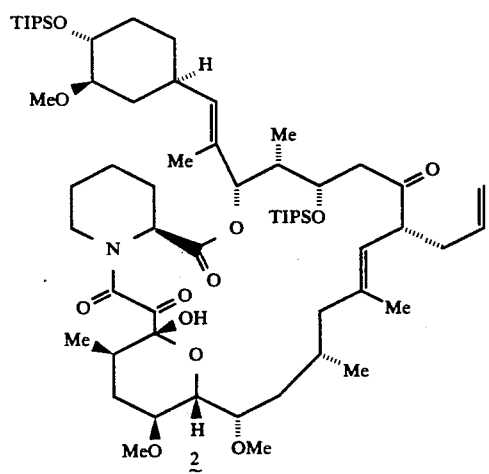

b) contacting followed by methanolic K$_2$CO$_3$ 2 with Pb(OAc)$_4$ to form 3;

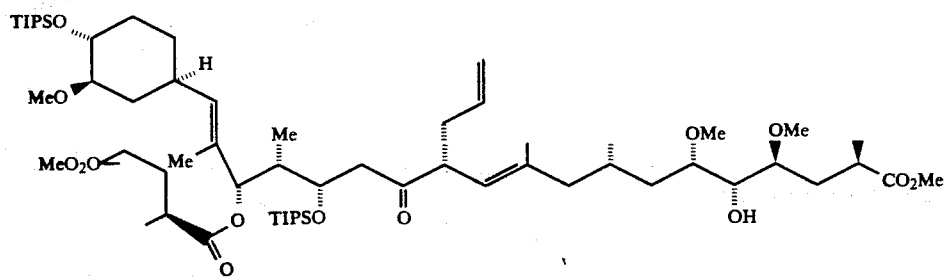

c) contacting 3 with t-butyldimethylsilyl triflate in dry dichloromethane at 0°–10° C. in the presence of an organic amine hydrogen acceptor to form 5;

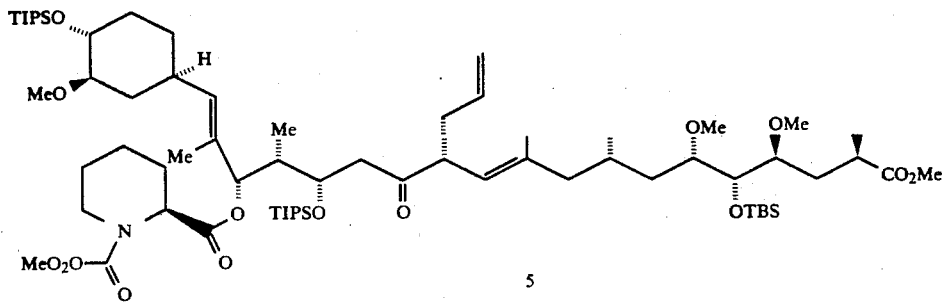

5 d) contracting 5 with LiAlH₄ in THF at 0°–5° C. for a sufficient time to form the triols 6 (R/S);

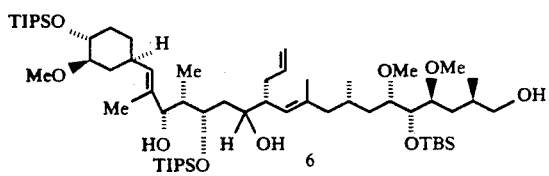

6 e) contacting the triols 6 (R/S) with triethylsilylchloride in dry pyridine at −10° C. to 0° C. for a sufficient time to form the alcohol 7 (R/S);

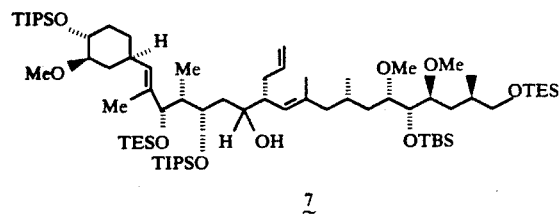

7 f) contacting alcohols 7 (R/S) with t-butyldimethylsilyl triflate in a dry organic solvent in the presence of an organic amine hydrogen acceptor at a temperature in the range of 0°–10° C. for a sufficient time to form the ethers 8 (R/S);

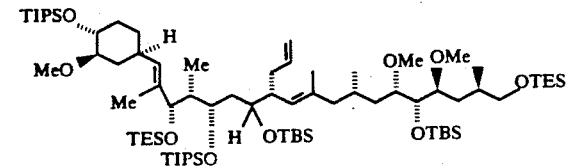

8 g) contacting 8 with acetic acid to form the C-10 primary alcohols 9, 22(S) and 22(R);

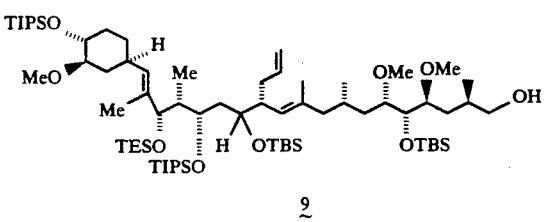

9 h) contacting 9 with oxalyl chloride, DMSO and an organic amine in a dry inert organic solvent at a temperature in the range of about −80° to −60° C. for a sufficient time to form 10;

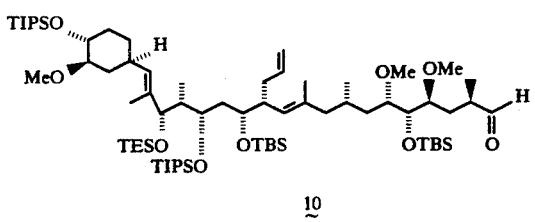

10 i) contacting 10 with methanol, trialkylorothoformate and pyridinium p-toluenesulfonate at 0°–10° C. in a dry organic solvent for a sufficient time to form 11;

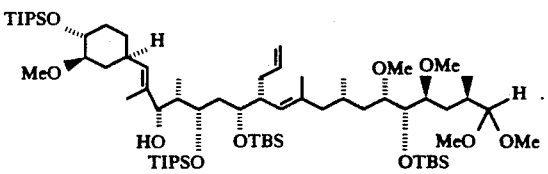

11

* * * * *